(12) United States Patent
Daraio et al.

(10) Patent No.: US 10,345,153 B2
(45) Date of Patent: Jul. 9, 2019

(54) GEL BASED THERMAL SENSORS

(71) Applicant: CALIFORNIA INSTITUTE OF TECHNOLOGY, Pasadena, CA (US)

(72) Inventors: Chiara Daraio, Zurich (CH); Raffaele Di Giacomo, Zurich (CH); Bruno Maresca, Fisciano (IT); Luca Bonanomi, Zurich (CH); Vincenzo Costanza, Zurich (CH)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/560,971

(22) PCT Filed: Mar. 24, 2016

(86) PCT No.: PCT/EP2016/056642
§ 371 (c)(1),
(2) Date: Sep. 22, 2017

(87) PCT Pub. No.: WO2016/151110
PCT Pub. Date: Sep. 29, 2016

(65) Prior Publication Data
US 2018/0080830 A1 Mar. 22, 2018

(30) Foreign Application Priority Data

Mar. 26, 2015 (EP) .................................... 15161042
Nov. 20, 2015 (EP) .................................... 15195729

(51) Int. Cl.
*G01J 5/00* (2006.01)
*G01J 5/04* (2006.01)
(Continued)

(52) U.S. Cl.
CPC ................. *G01J 5/046* (2013.01); *G01J 5/20* (2013.01); *G01J 5/24* (2013.01)

(58) Field of Classification Search
CPC ..................................... G01J 5/046; G01J 5/20
See application file for complete search history.

(56) References Cited

U.S. PATENT DOCUMENTS

| 5,834,776 A | 11/1998 | Beratan et al. |
| 9,274,004 B2 | 3/2016 | Yonemura et al. |
(Continued)

FOREIGN PATENT DOCUMENTS

| CN | 104075813 A | 10/2014 |
| CN | 107690571 A | 2/2018 |
(Continued)

OTHER PUBLICATIONS

Alamusi, "Temperature-Dependent Piezoresistivity in an MWCNT/Epoxy Nanocomposite Temperature Sensor with Ultrahigh Performance", Nanotechnology 24(45), 455501; 6 pages, (2013).
(Continued)

*Primary Examiner* — Yara B Green
(74) *Attorney, Agent, or Firm* — Steinfl + Bruno LLP

(57) ABSTRACT

A temperature sensor is described, which includes a sensor gel having a polymer, water and ions, and a first and a second electrode separated from each other by the sensor gel. The present disclosure further relates to a system which has a temperature sensor, a voltage source or electric current source, and a measurement device for detecting voltage or electric current. The present disclosure further relates to a bolometer and a temperature sensor array. A method for temperature detection is also described, wherein a temperature sensor is provided, a voltage or an electric current between the first electrode and the second electrode of the temperature sensor is provided, an electric current or a voltage between the first electrode and the second electrode is measured, and a temperature is determined from the measured electric current or voltage.

31 Claims, 15 Drawing Sheets

(51) Int. Cl.
G01J 5/20 (2006.01)
G01J 5/24 (2006.01)

(56) References Cited

U.S. PATENT DOCUMENTS

2007/0295907 A1 12/2007 Brott et al.
2013/0279538 A1* 10/2013 Beratan .................. G01J 5/046
374/165

FOREIGN PATENT DOCUMENTS

| EP | 3073235 A1 | 9/2016 |
| EP | 3274677 | 1/2018 |
| WO | WO 03/050522 * | 6/2003 |
| WO | 2016/151110 A1 | 9/2016 |

OTHER PUBLICATIONS

Cardoso, S.M. et al., "Temperature Dependence of the Formation and Melting of Pectin-Ca 2+ Networks: A Rheological Study", Food Hydrocolloids 17(6), pp. 801-807, (2003).
Di Giacomo, R. et al., "Bio-Nano-Composite Materials Constructed with Single Cells and Carbon Nanotubes: Mechanical, Electrical, and Optical Properties", IEEE Trans Nano Technol. 12(6), pp. 1026-1030, (2013).
Di Giacomo, R. et al., "Candida Albicans/MWCNTs: A Stable Conductive Bio-Nano-Composite and its Temperature Sensing Properties", IEEE Trans Nano Technol. 12(2), pp. 111-114, (2013).
Di Giacomo, R. et al., "Plant Nanobionic Materials with a Giant Temperature Response Mediated by Pectin-$Ca^{2+}$", Proceedings of the National Academy of Sciences, vol. 112, No. 15, pp. 4541-4545, (2015).
Fensom, D.S., "On Measuring Electrical Resistance in Situ in Higher Plants", Can. J. Plant Sci. 46(2), pp. 169-175, (1966).
Giraldo, J.P. et al., "Plant Nanobionics Approach to Augment Photosynthesis and Biochemical Sensing", Nat Mater 13(4), pp. 400-408, (2014).
Han, Jin-Woo, et al., "Carbon Nanotube Based Humidity Sensor on Cellulose Paper", J. Phys. Chem. C 116(41), pp. 22094-22097, (2012).
Itkis, M.E. et al., "Bolometric Infrared Photoresponse of Suspended Single-Walled Carbon Nanotube Films", Science 312(5772), pp. 413-416, (2006).
Kaltenbrunner, M. et al., "An Ultra-Lightweight Design for Imperceptible Plastic Electronics", Nature 499, pp. 458-463, (2013).
Keplinger, C. et al., "Stretchable, Transparent, Ionic Conductors", Science 341, pp. 984-987, (2013).
Kim, J. et al., "Stretchable Silicon Nanoribbon Electronics for Skin Prosthesis", Nature Commun. 5:5747, 11 pages, (2014).
Li, C. et al., "Continuum Percolation of Nanocomposites with Fillers of Arbitrary Shapes", Appl Phys Lett 90:174108, 3 pages, (2007).
Li, X. et al., "Direct Measurements of Interactions Between Polypeptides and Carbon Nanotubes", J Phys Chem B 110(25), pp. 12621-12625, (2006).
McCrudden, M. et al., "Microneedle Applications in Improving Skin Appearance", Exp. Dermatol. 24, pp. 561-566, (2015).
Nilsson, M. et al., "Mesopore Structure of Microcrystalline Cellulose Tablets Characterized by Nitrogen Adsorption and SEM: The Influence on Water-Induced Ionic Conduction", J Phys Chem B 110(32), pp. 15776-15781, (2006).
Saha, D. et al., "Hydrocolloids as Thickening and Gelling Agents in Food: A Critical Review", J Food Sci. Technol. 47, pp. 587-597, (2010).
Segev-Bar, M. et al., "Tunable Touch Sensor and Combined Sensing Platform: Toward Nanoparticle-Based Electronic Skin", ACS Appl. Mater. Interfaces 5, pp. 5531-5541, (2013).

Simmons, J.G., "Generalized Formula for the Electric Tunnel Effect between Similar Electrodes Separated by a Thin Insulating Film", J Appl Phys 34, pp. 1793-1803, (1963).
Sriamornsak, P., "Chemistry of Pectin and Its Pharmaceutical Uses: A Review", Silpakorn Univ. Int. J. 3, pp. 206-228, (2003).
Stapleton, F. et al., "Silicone Hydrogel Contact Lenses and the Ocular Surface", Ocular Surface 4, pp. 24-43, (2006).
Vay, L. et al., "The Therm-TRP Ion Channel Family: Properties and Therapeutic Implications", British J. of Pharmacol. 165, pp. 787-801, (2012).
Willats, W. et al., "Pectin: Cell Biology and Prospects for Functional Analysis", Plant Mol. Biol. 47, pp. 9-27, (2001).
PCT International Search Report for PCT/EP2016/056642 filed Mar. 24, 2016 on behalf of Eth Zürich, dated Jun. 27, 2016. 3 pages.
PCT Written Opinion for PCT/EP2016/056642 filed Mar. 24, 2016 on behalf of Eth Zürich, dated Jun. 27, 2016. 6 pages.
Balberg, "Tunneling and Nonuniversal Conductivity in Composite Materials." Phys Rev Lett 59(12); pp. 1305-1308; (Sep. 1987).
Di Giacomo et al., "Investigation of Multiwalled Carbon Nanotube Interconnection Geometry and Electrical Characteristics of an CNT-Filled Aluminum Microgap.", Can J Phys 92(7/8); pp. 827-831; (Jan. 2014).
Itkis et al., "Thermal Conductivity Measurements of Semitransparent Single-Walled Carbon Nanotube Films by a Bolometric Technique", Nano Lett 7(4); pp. 900-904; (Mar. 2007).
Jong et al., "Solvatochromism in Single-Walled Carbon Nanotubes.", Appl Phys Lett 90:223114; (May 2007).
Matthews et al., "High Temperature Behavior of Cellulose I.", J Phys Chem B 115(10); pp. 2155-2166; (Feb. 2011).
Miquel et al., "Thermoresponsive Chitosan-Agarose Hydrogel for Skin Regeneration.", Carb. Polym. 111; pp. 366-373; (May 2014).
Nadel et al., "Differential Thermal Sensitivity in the Human Skin.", Pflugers Arch. 340, pp. 71-76; (Received Apr. 1972—Published 1973).
Nilsson et al., "Water-Induced Charge Transport in Tablets of Microcrystalline Cellulose of Varying Density: Dielectric Spectroscopy and Transient Current Measurements.", Chem Phys 295(2); pp. 159-165; (Sep. 2003).
Nilsson et al., "Conductivity Percolation in Loosely Compacted Microcrystalline Cellulose: An in situ Study by Dielectric Spectroscopy During Densification." J Phys Chem B 110(41); pp. 20502-20506; (Sep. 2006).
Neitzert et al., "EPOXY/MWCNT Composite as Temperature Sensor and Electrical Heating Element.", IEEE Trans NanoTechnol 10(4); pp. 688-693; (Jul. 2011).
Plazinski, "Molecular Basis of Calcium Binding by Polyguluronate Chains. Revising the Egg-box model.", J Comput. Chem. 32; pp. 2988-2995; (Jul. 2011).
Qi et al., "Unique Water Sensors Based on Carbon Nanotube-Cellulose Composites.", Sens Actuators B Chem 185; pp. 225-230; (May 2013).
Sun et al., "Ionic Skin.", Adv. Mater. 26, pp. 7608-7614; (2014).
Tee et al., "An Electronically and Mechanically Self-Healing Composite with Pressure-and Flexion-Sensitive Properties for Electronic Skin Applications.", Nature Nanotech. 7; pp. 825-832; (Nov. 2012).
Wilson, "Giant impacts may explain the origin of chondrules", Phys. Today 68;15; pp. 14-17 (Mar. 2015).
First Chinese OA Application No. 201680030032.3 filed Mar. 24, 2016 in the name of California Institute of Technology. dated Jan. 22, 2019. 22 pgs. Chinese and English.
Bockrath et al. "Luttinger-liquid behavior in carbon nanotubes" Nature, Macmillan Magazines Ltd. Feb. 18, 1999. vol. 397. pp. 598-601. 4 pages.
Caffall et al. "The structure, function, and biosynthesis of plant cell wall pectic polysaccharides" Carbohydrate Research, Elsevier. 2009. vol. 344. pp. 1879-1900. 22 pages.
Cifuentes et al. "Biosynthesis of Callose and Cellulose by Detergent Extracts of Tobacco Cell Membranes and Quantification of the Polymers Synthesized in vitro" Journal of Integrative Plant Biology, Chinese Academy of Sciences—Institute of Botany. 2010. vol. 52, No. 2. pp. 221-233. 13 pages.

(56) References Cited

OTHER PUBLICATIONS

Fensom, D.S. "A Note on Electrical Resistance Measurements in Acer Saccharum" *Canadian Journal of Botany, NRC Research Press.* 1960. vol. 38, No. 2. pp. 263-265. 5 pages.

Fernandes et al. "Nanostructure of cellulose microfibrils in spruce wood" *Proceedings of the National Academy of Sciences, National Academy of Sciences.* Nov. 22, 2011. vol. 108, No. 47. pp. E1195-E1203. 9 pages.

Guerette et al. "Accelerating the design of biomimetic materials by integrating RNA-seq with proteomics and materials science" Nature Biotechnology, Nature America Inc. Oct. 2013. vol. 31, No. 10. pp. 908-915. 11 pages.

Hu et al. "Localization of Boron in Cell Walls of Squash and Tobacco and Its Association with Pectin—Evidence for a Structural Role of Boron in the Cell Wall" *Plant Physiology, American Society of Plant Biologists.* 1994. vol. 105. pp. 681-689. 9 pages.

International Preliminary Report on Patentability for International Application No. PCT/EP2016/056642, filed on Mar. 24, 2016, on behalf of California Institute of Technology. dated Sep. 26, 2017. 7 pages.

Kamaya et al. "A lithium superionic conductor" *Nature Materials, Macmillan Publishers Ltd.* Sep. 2011. vol. 10. pp. 682-686. 5 pages.

Leslie et al. "A bioinspired omniphobic surface coating on medical devices prevents thrombosis and biofouling" *Nature Biotechnology, Nature America Inc.* Nov. 2014. vol. 32, No. 11. pp. 1134-1140. 10 pages.

Li et al. "Dominant role of tunneling resistance in the electrical conductivity of carbon nanotube-based composites" *Applied Physics Letters, American Institute of Physics.* 2007. vol. 91. pp. 223114-1-223114-3. 4 pages.

Narayan et al. "Phase transition and critical issues in structure-property correlations of vanadium oxide" *Journal of Applied Physics, American Institute of Physics.* 2006. vol. 100. pp. 103524-1-103524-6. 7 pages.

Nawroth et al. "A tissue-engineered jellyfish with biomimetic propulsion" *Nature Biotechnology, Nature Publishing Group.* Aug. 2012. vol. 30, No. 8. pp. 792-797. 20 pages.

Peaucelle et al. "Cell wall mechanics and growth control in plants: the role of pectins revisited" *Frontiers in Plant Science, Frontiers Media.* Jun. 2012. vol. 3, No. 121. pp. 1-6. 6 pages.

Sheng, Ping. "Flactuation-induced tunneling conduction in disordered materials" *Physica/ Review B, The American Physical Society.* Mar. 15, 1980. vol. 21, No. 6. pp. 2180-2195. 16 pages.

Syllaios et al. "Amorphous Silicon Microbolometer Technology" *Materials Research Society Symposium Proceedings, Materials Research Society.* 2000. vol. 609. pp. A14.4.1-A14.4.6. 8 pages.

Tan et al. "Studies on toxicity of multi-walled carbon nanotubes on suspension rice cells" *Carbon, Elsevier.* 2009. vol. 47. pp. 3479-3487. 9 pages.

Thomas et al. "Structure of Cellulose Microfibrils in Primary Cell Walls from Collenchyma" *Plant Physiology, American Society of Plant Biologists.* Jan. 2013. vol. 161. pp. 465-476. 12 pages.

Van Buren, J.P. "Chapter 1: Function of Pectin in Plant Tissue Structure and Firmness" *The Chemistry and Technology of Pectin, Academic Press Inc.* 1991. pp. 1-23. 15 pages.

Vollmer et al. "Infrared Thermal Imaging: Fundamentals, Research and Applications" *Wiley-VCH Verlag GmbH & Co. KGaA.* 2010. pp. i-593. 611 pages.

Wang et al. "Nanostructured vanadium oxide thin film with high TCR at room temperature for microbolometer" *Infrared Physics & Technology, Elsevier.* 2013. vol. 57. pp. 8-13. 7 pages.

\* cited by examiner

GEL BASED THERMAL SENSORS

CROSS REFERENCE TO RELATED APPLICATIONS

The present application is the US national stage of International Application No. PCT/EP2016/056642 filed on Mar. 24, 2016 which, in turn, claims priority to European application No. 15161042.5 filed on Mar. 26, 2015 and European application No. 15195729.7 filed on Nov. 20, 2015, the contents of each of which are incorporated by reference in their entireties.

FIELD OF INVENTION

The present invention relates to a temperature sensor comprising a polymer gel.

BACKGROUND OF THE INVENTION

Materials that respond sensitively to temperature variations are used in several applications that range from electrical temperature sensors to micro bolometers for thermal cameras.

Existing high-performance temperature-sensitive materials, such as vanadium oxide, have temperature coefficients of electrical resistance (TCR) on the order of −6% $K^{-1}$ at room temperature. These materials derive their properties from changes of their crystal structure during semiconductor to metal transitions.

Variations of the ambient temperature influence the biopotential of living plants. Experiments performed in vivo on a maple tree (*Acer saccharum*) showed an exponential correlation between the tree's branch electrical resistance and temperature. This behaviour has been attributed to ionic conductivity occurring in plant cell walls.

The plant cell wall, positioned outside the plasma membrane, is composed of carbohydrates such as cellulose microfibrils with diameters as small as 3.0 nm, and hemicellulose interconnected with pectin. Pectins are composed of pectic polysaccharides rich in galacturonic acid that influence properties such as porosity, surface charge, pH, and ion balance and therefore are critical for ion transport within the cell wall. Pectins contain multiple negatively charged saccharides that bind cations, such as $Ca^{2+}$, that form cross-links that confer strength and expansibility to the cell wall. It has been shown that the gelation rate of pectin decreases exponentially with temperature so that the number of dissociated chains is higher at elevated temperatures. This finding is explained by an entropic effect: as the temperature increases, the probability of interaction between two pectin chains is reduced (Cardoso et al. (2003), *Food Hydrocoll* 17(6):801-807).

Here, we utilized the exceptionally high temperature- and moisture sensitivity of biopolymers and related materials to develop temperature and humidity sensors with unique properties.

The objective of the present invention is to provide a temperature sensor comprising a polymer gel.

This objective is attained by the subject-matter of the independent claims.

Terms and Definitions

In the context of the present specification, the term "ion" describes an atom or a molecule in which the total number of electrons is unequal to the total number of protons, which results in a positive or negative electric net charge of the atom or molecule.

In the context of the present specification, the terms "voltage" is used in its meaning known in the art of physics. It refers to the electrical potential in either alternating current (AC) or direct current (DC) regime.

In the context of the present specification, the terms "current" is used in its meaning known in the art of physics. It refers to either AC or DC.

In the context of the present specification, the terms "voltage source" or "current source" refer either to AC or DC sources.

In the context of the present specification, the term "electrical impedance" is used in its meaning known in the art of physics. It refers to the complex ratio of the voltage to the current in an AC circuit.

In the context of the present specification, the term "electrical resistance" is used in its meaning known in the art of physics. It refers to the ratio of the voltage to the current in a DC circuit.

In the context of the present specification, the term "electrical conductivity" is used in its meaning known in the art of physics. It refers to the ratio of the current to the voltage in a DC.

In the context of the present specification, the term "bolometer" describes a device adapted to measure electromagnetic radiation, particularly infrared radiation, over a distance of more than 10 cm, particularly more than 1 m. The term "bolometer" comprises "micro bolometers".

In the context of the present specification, the term "micro bolometer" describes a bolometer having a maximal extension of less than 10 μm, particularly less than 5 μm, more particularly less than 2 μm.

In the context of the present specification, the term "micro temperature sensor" describes a temperature sensor having a maximal extension of less than 10 μm, particularly less than 5 μm, more particularly less than 2 μm.

In the context of the present specification, the term "micro humidity sensor" describes a humidity sensor having a maximal extension of less than 10 μm, particularly less than 5 μm, more particularly less than 2 μm.

In the context of the present specification, the term "hydrogel" refers to a network of polymer chains that are hydrophilic.

In the context of the present specification, the term "polymer" refers to a molecule, which is composed of repeated subunits, wherein the subunits are connected by covalent bonds.

In the context of the present specification, the term "charged moiety" describes a group of atoms having a positive or negative charge.

In the context of the present specification, the term "polyelectrolyte" refers to a polymer comprising a charged moiety.

In the context of the present specification, the term "biopolymer" refers to a biomolecule, which is also a polymer, particularly selected from polysaccharides, peptides, polypeptides, proteins, deoxyribonucleic acids (DNA), or ribonucleic acids (RNA).

In the context of the present specification, the term "pectin" refers to a heteropolysaccharide comprising galacturonic acid subunits. In the context of the present specification, a substance described by the term "pectin" may comprise methyl esterified carboxyl groups.

The following common chemical terms are known to the person skilled in the art and defined in case of ambiguity by their Chemical Abstract Services Identifier Number (CAS):

Alginate: CAS 9005-38-3; amylose: CAS 9005-82-7, amylopectin: CAS 9037-22-3; carboxymethyl cellulose: CAS 9004-32-4; cellulose: CAS 9004-34-6; chitin: CAS 1398-61-4; chitosan: CAS 9012-76-4; dextran: CAS 9004-54-0; glycogen: CAS 9005-79-2; guaran: CAS 9000-30-0; hyaluronic acid: CAS 9067-32-7; polyacrylic acid: CAS 9003-01-4; polysterene sulfonate: CAS 28210-41-5; polyethylene (PE): CAS 9002-88-4; polypropylene (PP): CAS 9003-07-0; polysterene (PS): CAS 9003-53-6; polymethyl methacrylate (PMMA): CAS 9011-14-7; polyvinyl chloride (PVC): CAS 9002-86-2; polyvinylidene fluoride (PVDF): CAS 24937-79-9

SUMMARY OF THE INVENTION

According to a first aspect of the invention, a temperature sensor comprising a sensor gel is provided, wherein the sensor gel comprises a polymer, water (at a weight portion of 0.1% or more), and ions that can move within the sensor gel and can particularly bind to charged moieties on the polymer, wherein the concentration of the ions is 1 pM or more. The temperature sensor further comprises a first electrode and a second electrode, wherein the first electrode and the second electrode are separated from each other by the sensor gel.

In particular, the sensor gel is adapted to transport an electric current from the first electrode to the second electrode, wherein the electric current is dependent on the temperature of the sensor gel.

In certain embodiments, the temperature sensor is a micro temperature sensor.

In certain embodiments, the ionic conductivity of the sensor gel changes with temperature.

In certain embodiments, the electrical impedance or electrical resistance of the sensor gel changes with temperature.

In certain embodiments, the sensor gel comprises a hydrogel.

In certain embodiments, the polymer is a polyelectrolyte.

In certain embodiments, the polymer is selected from a charged biopolymer, particularly a peptide, a polypeptide, or a polysaccharide comprising charged moieties, more particularly pectin, alginate, or alginate sulfate, and/or a synthetic polymer having charged moieties, particularly polyacrylic acid, polysterene sulfonate, a cationic derivative of hyaluronic acid, or carboxymethyl cellulose.

In certain embodiments, the sensor gel comprises a network of polymers, wherein the network is constituted by covalent bonds, and/or ionic bonds, and/or physical crosslinks.

In certain embodiments, the polymer is selected from an uncharged polysaccharide, particularly agarose, amylose, amylopectin, callose, cellulose, chitin, chitosan, dextran, glycogen, guaran, or hemicellulose, or an uncharged peptide or polypeptide.

In certain embodiments, the polymer is selected from a synthetic polymer, particularly polyethylene (PE), polypropylene (PP), polysterene (PS), polymethyl methacrylate (PMMA), polyvinyl chloride (PVC), and/or polyvinylidene fluoride (PVDF).

In certain embodiments, the ions have a charge of 2 or greater.

In certain embodiments, the ions have a charge of 3.
In certain embodiments, the ions have a charge of 4.
In certain embodiments, the ions are divalent ions.

In certain embodiments, the sensor gel is crosslinked by the divalent ions.

In certain embodiments, the ions are metal ions.
In certain embodiments, the sensor gel is crosslinked by the metal ions.

In certain embodiments, the ions are $Ca^{2+}$, $Mg^{2+}$, $Cu^{2+}$, $Sr^{2+}$, or $Ba^{2+}$ ions, particularly $Ca^{2+}$ ions.

In certain embodiments, the polymer is pectin.
In certain embodiments, the polymer is pectin comprising methyl esterified carboxyl groups.

Advantageously, hydrogels comprising pectin and $Ca^{2+}$ ions display an especially high effective temperature coefficient of electrical resistance (TCR).

In certain embodiments, the pectin is crosslinked by the ions, particularly divalent ions and/or metal ions, more particularly cations.

In certain embodiments, the pectin is crosslinked by $Ca^{2+}$, $Mg^{2+}$, $Cu^{2+}$, $Sr^{2+}$, or $Ba^{2+}$ ions, particularly $Ca^{2+}$ ions.

In certain embodiments, the pectin is crosslinked by $Ca^{2+}$ ions.

In certain embodiments, the sensor gel comprises cell walls from plant cells, particularly tobacco plants, more particularly *Nicotiana tabacum*, most particularly BY-2 cells.

In certain embodiments, the sensor gel comprises plant cells, particularly tobacco plants, more particularly *Nicotiana tabacum*, most particularly BY-2 cells.

Advantageously, BY-2 cells are easy to cultivate and exhibit fast growth.

In certain embodiments, the sensor gel comprises carbon nanotubes, particularly multiwalled carbon nanotubes (MWCNTs).

Advantageously, MWCNTs have been observed to increase the lifespan of sensor gels.

In certain embodiments, the sensor gel comprises graphite.

In certain embodiments, the sensor gel has a water content of <60%, particularly <40%, more particularly <30% weight per volume.

Advantageously, a water content below 40% has been shown to positively influence the temperature sensitivity of electrical resistance of the sensor gel.

In certain embodiments, the sensor gel has a water content of <25%, particularly <20%, more particularly <15% weight per volume.

In certain embodiments, the stoichiometric ratio of ions to charged moieties is 1:1000 to 3:1, particularly 1:100 to 3:1, more particularly 1:10 to 3:1, most particularly 1:1.

In certain embodiments, the sensor gel is a cell free gel.
In certain embodiments, the sensor gel is essentially composed of the polymer, water, and ions, particularly wherein the sensor gel is free from carbon nanotubes.

Advantageously, such sensor gels are easy to prepare and require only low-cost reagents.

In certain embodiments the first electrode and/or the second electrode comprises carbon.

In certain embodiments the first electrode and/or the second electrode comprises platinum.

In certain embodiments, the sensor gel comprises pectin at a concentration of 60% to 99% in weight, particularly 70% in weight.

In certain embodiments, the sensor gel comprises pectin having a degree of methylation of 10% to 90%, particularly 34%.

In certain embodiments, the pectin has a content of galacturonic acid of 70% to 90%, particularly 84%.

In certain embodiments, in the temperature sensor as described in the preceding aspect and its distinct embodiments, water is substituted by another solvent for ions, or an additional solvent for ions.

In certain embodiments, water is substituted by an ionic conductor.

In certain embodiments, water is substituted by a liquid electrolyte.

In certain embodiments, water is substituted by a solid electrolyte.

In certain embodiments, the sensor gel is embedded in a casing that is not permeable to liquid water and/or water vapour.

In certain embodiments, the casing is transparent to infrared radiation, particularly in the wavelength range of 3 μm to 50 μm.

In certain embodiments, the casing is transparent to mid or far infrared radiation.

In certain embodiments, the casing comprises germanium.

In certain embodiments, the casing comprises polydimethylsiloxane (PDMS).

In certain embodiments, the casing comprises cellophane.

Advantageously, encasing the sensor gel eliminates humidity effects on the conductivity of the sensor gel.

In certain embodiments, the first electrode, and/or the second electrode is made of a material selected from the group consisting of copper, silver, gold and aluminium.

In certain embodiments, the first electrode, and/or the second electrode is made of a material selected from the group consisting of platinum, carbon, steel, polysilicon, chromium, and niobium.

According to a second aspect of the invention, a system comprising a temperature sensor according to the first aspect of the invention, a voltage source or electric current source, and a measurement device for detecting voltage or current is provided. Therein the temperature sensor and the measurement device are electrically connected, such that an electric current through the temperature sensor, or a voltage between the first electrode and the second electrode of the temperature sensor is measurable by the measurement device.

In certain embodiments, the system comprises a voltage source and the measurement device is an ampere meter for detecting electric current, wherein the temperature sensor and the ampere meter are electrically connected, such that an electric current through the temperature sensor is measurable by the ampere meter.

In certain embodiments, the system comprises a voltage source and an electrical circuit for detecting electric current, wherein the temperature sensor and the electrical circuit are electrically connected, such that an electric current through the temperature sensor is measurable by the electrical circuit.

In certain embodiments, the system comprises a current source and an electrical circuit for detecting voltage, wherein the temperature sensor and the electrical circuit are electrically connected, such that a voltage between the first electrode and the second electrode of the temperature sensor is measurable by the electrical circuit.

In certain embodiments, the system comprises two or more temperature sensors, wherein the temperature sensors are connected in series.

In certain embodiments, the system comprises two or more temperature sensors, wherein the temperature sensors are connected in parallel.

According to a third aspect of the invention, a bolometer, particularly a mid or far infrared detector is provided, wherein the bolometer comprises a temperature sensor according to the first aspect of the invention.

In certain embodiments, the bolometer is a micro bolometer.

According to a fourth aspect of the invention, a temperature sensor array comprising a plurality of sections arranged in a two-dimensional array is provided. Therein each section comprises a respective temperature sensor according to the first aspect of the invention, and the temperature of each section is determinable by means of the respective temperature sensor.

According to a fifth aspect of the invention, a method for temperature detection by means of a temperature sensor according to the first aspect of the invention is provided. Therein, the method comprises the steps of providing a temperature sensor according to the first aspect of the invention, providing a voltage or an electric current between the first electrode and the second electrode of the temperature sensor, measuring an electric current or a voltage between the first electrode and the second electrode, and determining a temperature from the measured electric current or voltage.

In certain embodiments, the method comprises providing a voltage between the first electrode and the second electrode of the temperature sensor, and measuring an electric current between the first electrode and the second electrode, particularly by means of an ampere meter, wherein the temperature sensor and the ampere meter are electrically connected.

In certain embodiments, the method comprises providing an electric current between the first electrode and the second electrode of the temperature sensor, and measuring a voltage between the first electrode and the second electrode, particularly by means of an electronic circuit, wherein the temperature sensor and the electronic circuit are electrically connected.

In certain embodiments the electric current is converted into a voltage by means of an electronic circuit.

In certain embodiments, infrared radiation of an object is detected by means of the temperature sensor.

According to a sixth aspect of the invention, a method for obtaining a sensor gel is provided, wherein the method comprises the steps of providing a mixture comprising a gel-forming substance and ions, wherein the mixture is free from plant cells, and reducing the water content of the mixture, particularly to 60%, more particularly 40%, even more particularly 30%.

In certain embodiments, the ions are divalent ions.

In certain embodiments, the ions are metal ions.

In certain embodiments, the ions are $Ca^{2+}$ ions.

In certain embodiments, the gel forming substance is pectin.

In certain embodiments, the gel forming substance is pectin comprising methyl esterified carboxyl groups.

In certain embodiments, the pectin is provided in purified form, particularly at a concentration of 1% to 3% weight per volume, particularly 2% weight per volume, in order to prepare the mixture.

In certain embodiments, the pectin has a degree of methylation of 10% to 90%, particularly 34%.

In certain embodiments, the pectin has a content of galacturonic acid of 10% to 90%, particularly 84%.

In certain embodiments, the stoichiometric ratio of the ions to the gel forming substance is 1:1000 to 3:1, particularly 1:100 to 3:1, more particularly 1:10 to 3:1, most particularly 1:1.

According to a seventh aspect of the invention, a method for obtaining a sensor gel is provided, wherein the method comprises the steps of providing a mixture comprising a suspension of plant cells, particularly from tobacco plants, more particularly from *Nicotiana tabacum*, most particularly BY-2 cells, and reducing the water content of the mixture.

In certain embodiments, the mixture comprises carbon nanotubes, particularly multiwalled carbon nanotubes (MW-CNTs).

According to an eighth aspect of the invention, a humidity sensor comprising a sensor gel is provided, wherein the sensor gel comprises a polymer. The humidity sensor further comprises a first electrode and a second electrode, wherein the first electrode and the second electrode are separated from each other by the sensor gel.

In particular, the sensor gel is adapted to transport an electric current from the first electrode to the second electrode, wherein the electric current is dependent on the humidity of the sensor gel.

In certain embodiments, the humidity sensor is a micro humidity sensor.

In certain embodiments, the conductivity of the sensor gel changes with humidity.

In certain embodiments, the electrical impedance or electrical resistance of the sensor gel changes with humidity.

In certain embodiments, the sensor gel comprises a hydrogel.

In certain embodiments, the polymer is a polyelectrolyte.

In certain embodiments, the polymer is selected from a charged biopolymer, particularly a peptide, a polypeptide, or a polysaccharide comprising charged moieties, more particularly pectin, alginate, or alginate sulfate, and/or a synthetic polymer having charged moieties, particularly polyacrylic acid, polysterene sulfonate, a cationic derivative of hyaluronic acid, or carboxymethyl cellulose.

In certain embodiments, the sensor gel comprises a network of polymers, wherein the network is constituted by covalent bonds, and/or ionic bonds, and/or physical crosslinks.

In certain embodiments, the polymer is selected from an uncharged polysaccharide, particularly agarose, amylose, amylopectin, callose, cellulose, chitin, chitosan, dextran, glycogen, guaran, or hemicellulose, or an uncharged peptide or polypeptide.

In certain embodiments, the polymer is selected from a synthetic polymer, particularly polyethylene (PE), polypropylene (PP), polysterene (PS), polymethyl methacrylate (PMMA), polyvinyl chloride (PVC), and/or polyvinylidene fluoride (PVDF).

In certain embodiments, the sensor gel is crosslinked by ions.

In certain embodiments, the sensor gel is crosslinked by divalent ions.

In certain embodiments, the sensor gel is crosslinked by metal ions.

In certain embodiments, the sensor gel is crosslinked by $Ca^{2+}$, $Mg^{2+}$, $Cu^{2+}$, $Sr^{2+}$, or $Ba^{2+}$ ions, particularly $Ca^{2+}$ ions.

In certain embodiments, the polymer is pectin.

In certain embodiments, the polymer is pectin comprising methyl esterified carboxyl groups.

In certain embodiments, the pectin is crosslinked by the ions, particularly divalent ions and/or metal ions, more particularly cations.

In certain embodiments, the pectin is crosslinked by $Ca^{2+}$, $Mg^{2+}$, $Cu^{2+}$, $Sr^{2+}$, or $Ba^{2+}$ ions, particularly $Ca^{2+}$ ions.

In certain embodiments, the sensor gel comprises cell walls from plant cells, particularly from tobacco plants, more particularly from *Nicotiana tabacum*, most particularly BY-2 cells.

In certain embodiments, the sensor gel comprises plant cells, particularly tobacco plants, more particularly *Nicotiana tabacum*, most particularly BY-2 cells.

In certain embodiments, the sensor gel comprises carbon nanotubes, particularly multiwalled carbon nanotubes (MW-CNTs).

In certain embodiments, the sensor gel is a cell free gel.

In certain embodiments, the sensor gel is essentially composed of the polymer, water, and ions, particularly wherein the sensor gel does not contain carbon nanotubes.

In certain embodiments, the sensor gel comprises pectin at a concentration of 1% to 3% weight per volume, particularly 2% weight per volume.

In certain embodiments, the sensor gel comprises pectin having a degree of methylation of 10% to 90%, particularly 34% weight per weight.

In certain embodiments, the pectin has a content of galacturonic acid of 10% to 90%, particularly 84% weight per weight.

In certain embodiments, the first electrode, and/or the second electrode is made of a material selected from the group consisting of copper, silver, gold, and aluminium.

In certain embodiments, the first electrode, and/or the second electrode is made of a material selected from the group consisting of platinum, carbon, steel, polysilicon, chromium, and niobium.

According to a tenth aspect of the invention, a system comprising a humidity sensor according to the ninth aspect of the invention, and a measurement device for detecting voltage or current is provided. Therein the humidity sensor and the measurement device are connected, such that an electric current through the humidity sensor or a voltage between the first electrode and the second electrode of the humidity sensor is measurable by the measurement device.

In certain embodiments, the system comprises a voltage source and the measurement device is an ampere meter for detecting electric current, wherein the humidity sensor and the ampere meter are electrically connected, such that an electric current through the humidity sensor is measurable by the ampere meter.

In certain embodiments, the system comprises a voltage source and the measurement device is an electrical circuit for detecting electric current, wherein the humidity sensor and the electrical circuit are electrically connected, such that an electric current through the humidity sensor is measurable by the electrical circuit.

In certain embodiments, the system comprises a current source and an electrical circuit for detecting voltage, wherein the humidity sensor and the electrical circuit are electrically connected, such that a voltage between the first electrode and the second electrode of the humidity sensor is measurable by the electrical circuit.

In certain embodiments, the system comprises two or more humidity sensors, wherein the humidity sensors are connected in series.

In certain embodiments, the system comprises two or more humidity sensors, wherein the humidity sensors are connected in parallel.

According to an eleventh aspect of the invention, a method for humidity detection by means of a humidity sensor according to the ninth aspect of the invention is provided. Therein, the method comprises the steps of providing a humidity sensor according to the ninth aspect of the invention, providing a voltage or an electric current between the first electrode and the second electrode of the humidity sensor, measuring an electric current or a voltage between the first electrode and the second electrode, and determining a humidity from the measured electric current or voltage.

In certain embodiments, the method comprises providing a voltage between the first electrode and the second electrode of the humidity sensor, and measuring an electric current between the first electrode and the second electrode, particularly by means of an ampere meter, wherein the humidity sensor and the ampere meter are electrically connected.

In certain embodiments, the method comprises providing a voltage between the first electrode and the second electrode of the humidity sensor, and measuring an electric current between the first electrode and the second electrode, particularly by means of an electronic circuit, wherein the humidity sensor and the an electronic circuit are electrically connected.

In certain embodiments, the method comprises providing an electric current between the first electrode and the second electrode of the humidity sensor, and measuring a voltage between the first electrode and the second electrode, particularly by means of an electronic circuit, wherein the humidity sensor and the electronic circuit are electrically connected.

In certain embodiments the electric current is converted into a voltage by means of an electronic circuit.

Further alternative aspects and embodiments of the invention are specified in the following items: 1: A temperature sensor comprising a gel ionic conductor as a sensing element. 2: A temperature sensor comprising a gel comprising networks with covalent or ionic or physical crosslinks as a sensing element. 3: A temperature sensor comprising an hydrogel as a sensing element. 4: A temperature sensor comprising an aerogel as a sensing element. 5: A temperature sensor comprising pectin as a sensing element. 6: A temperature sensor comprising pectin crosslinked by calcium as a sensing element. 7: A temperature sensor comprising pectin crosslinked by metal ions as a sensing element. 8: A temperature sensor comprising pectin crosslinked by divalent ions as a sensing element. 9: A temperature sensor comprising pectin and calcium as a sensing element. 10: A temperature sensor comprising pectin and metal ions as a sensing element. 11: A temperature sensor comprising pectin and divalent ions as a sensing element. 12: A temperature sensor comprising hydrogel crosslinked by calcium as a sensing element. 13: A temperature sensor comprising hydrogel crosslinked by metal ions as a sensing element. 14: A temperature sensor comprising hydrogel crosslinked by divalent ions as a sensing element. 15: A temperature sensor comprising hydrogel and calcium as a sensing element. 16: A temperature sensor comprising hydrogel and metal ions as a sensing element. 17: A temperature sensor comprising hydrogel and divalent ions as a sensing element. 18: A temperature sensor comprising aerogel crosslinked by calcium as a sensing element. 19: A temperature sensor comprising aerogel crosslinked by metal ions as a sensing element. 20: A temperature sensor comprising aerogel crosslinked by divalent ions as a sensing element. 21: A temperature sensor comprising aerogel and calcium as a sensing element. 22: A temperature sensor comprising aerogel and metal ions as a sensing element. 23: A temperature sensor comprising aerogel and divalent ions as a sensing element. 24: A temperature sensor comprising gel crosslinked by calcium as a sensing element. 25: A temperature sensor comprising gel crosslinked by metal ions as a sensing element. 26: A temperature sensor comprising gel crosslinked by divalent ions as a sensing element. 27: A temperature sensor comprising gel and calcium as a sensing element. 28: A temperature sensor comprising gel and metal ions as a sensing element. 29: A temperature sensor comprising gel and divalent ions as a sensing element. 30: A device comprising one or more of the sensing elements of items 1 to 29 and two or more electrodes. 31: A device as said in item 30 wherein the said electrodes are made of a material selected from the group consisting of copper, silver, gold and aluminum. 32: A series of sensors according to any one of items 1 to 31. 33: Sensors in parallel according to any one of items 1 to 31. 34: Sensors in series and parallel according to any one of items 1 to 31. 35: A temperature sensor comprising two or more metallic electrodes and pectin crosslinked by calcium ions, enabled by the change of the electric impedance at the said metallic electrodes enabled by the changes in the ionic conductivity of the said pectin with temperature. 36: An electrical temperature sensor comprising a gel ionic conductor as a sensing element. 37: An electrical temperature sensor comprising a gel comprising networks with covalent or ionic or physical crosslinks as a sensing element. 38: An electrical temperature sensor comprising an hydrogel as a sensing element. 39: An electrical temperature sensor comprising an aerogel as a sensing element. 40: An electrical temperature sensor comprising pectin as a sensing element. 41: An electrical temperature sensor comprising pectin crosslinked by calcium as a sensing element. 42: An electrical temperature sensor comprising pectin crosslinked by metal ions as a sensing element. 43: An electrical temperature sensor comprising pectin crosslinked by divalent ions as a sensing element. 44: An electrical temperature sensor comprising pectin and calcium as a sensing element. 45: An electrical temperature sensor comprising pectin and metal ions as a sensing element. 46: An electrical temperature sensor comprising pectin and divalent ions as a sensing element. 47: An electrical temperature sensor comprising hydrogel crosslinked by calcium as a sensing element. 48: An electrical temperature sensor comprising hydrogel crosslinked by metal ions as a sensing element. 49: An electrical temperature sensor comprising hydrogel crosslinked by divalent ions as a sensing element. 50: An electrical temperature sensor comprising hydrogel and calcium as a sensing element. 51: An electrical temperature sensor comprising hydrogel and metal ions as a sensing element. 52: An electrical temperature sensor comprising hydrogel and divalent ions as a sensing element. 53: An electrical temperature sensor comprising aerogel crosslinked by calcium as a sensing element. 54: An electrical temperature sensor comprising aerogel crosslinked by metal ions as a sensing element. 55: An electrical temperature sensor comprising aerogel crosslinked by divalent ions as a sensing element. 56: An electrical temperature sensor comprising aerogel and calcium as a sensing element. 57: An electrical temperature sensor comprising aerogel and metal ions as a sensing element. 58: An electrical temperature sensor comprising aerogel and divalent ions as a sensing element. 59: An electrical temperature sensor comprising gel crosslinked by calcium as a sensing element. 60: An electrical temperature sensor comprising gel crosslinked by metal ions as a sensing element. 61: An electrical temperature sensor comprising gel crosslinked by divalent ions as a sensing element. 62: An electrical temperature sensor comprising gel and calcium as a sensing element. 63: An electrical temperature sensor comprising gel and metal ions as a sensing element. 64: An electrical temperature sensor comprising gel and divalent ions as a sensing element. 65: An electrical device comprising one or more of the sensing elements of items 36 to 64 and two or more electrodes. 66: An electrical device as said in item 65 wherein the said electrodes are made of a material selected from the group consisting of copper, silver, gold and aluminum. 67: An electrical series of sensors according to any one of items 36 to 66. 68: Sensors in parallel according to any one of items 36 to 66. 69: Sensors in series and parallel according to any one of items 36 to 66. 70: An electrical temperature sensor comprising two or more metallic electrodes and pectin crosslinked by calcium ions, enabled by the change of the electric impedance at the said metallic electrodes enabled by the changes in the ionic conductivity of the said pectin with temperature. 71: A mid or far infrared detector comprising a gel ionic conductor as a sensing element. 72: A mid or far infrared detector comprising a gel comprising networks with covalent or ionic or physical crosslinks as a sensing element. 73: A mid or far infrared detector comprising an hydrogel as a sensing element. 74: A mid or far infrared detector comprising an aerogel as a sensing element. 75: A mid or far infrared detector comprising pectin as a sensing element. 76: A mid or far infrared detector comprising pectin crosslinked by calcium as a sensing element. 77: A mid or far infrared detector comprising pectin crosslinked by metal ions as a sensing element. 78: A mid or far infrared detector comprising pectin crosslinked by divalent ions as a sensing element. 79: A mid or far infrared detector comprising pectin and calcium as a sensing element. 80: A mid or far infrared detector comprising pectin and metal ions as a sensing element. 81: A mid or far infrared detector comprising pectin and divalent ions as a sensing element. 82: A mid or far infrared detector comprising hydrogel crosslinked by calcium as a sensing element. 83: A mid or far infrared detector comprising hydrogel crosslinked by metal ions as a sensing element. 84: A mid or far infrared detector comprising hydrogel crosslinked by divalent ions as a sensing element. 85: A mid or far infrared detector comprising hydrogel and calcium as a sensing element. 86: A mid or far infrared detector comprising hydrogel and metal ions as a sensing element. 87: A mid or far infrared detector comprising hydrogel and divalent ions as a sensing element. 88: A mid or far infrared detector comprising aerogel crosslinked by calcium as a sensing element. 89: A mid or far infrared detector comprising aerogel crosslinked by metal ions as a sensing element. 90: A mid or far infrared detector comprising aerogel crosslinked by divalent ions as a sensing element. 91: A mid or far infrared detector comprising aerogel and calcium as a sensing element. 92: A mid or far infrared detector comprising aerogel and metal ions as a sensing element. 93: A mid or far infrared detector comprising aerogel and divalent ions as a sensing element. 94: A mid or far infrared detector comprising gel crosslinked by calcium as a sensing element. 95: A mid or far infrared detector comprising gel crosslinked by metal ions as a sensing element. 96: A mid or far infrared detector comprising gel crosslinked by divalent ions as a sensing element. 97: A mid or far infrared detector comprising gel and calcium as a sensing element. 98: A mid or far infrared detector comprising gel and metal ions as a sensing element. 99: A mid or far infrared detector comprising gel and divalent ions as a sensing element. 100: A device comprising one or more of the sensing elements of items 71 to 99 and two or more electrodes. 101: A device as said in item 100 wherein the said electrodes are made of a material selected from the group consisting of copper, silver, gold and aluminum. 102: A series of detectors according to any one of items 71 to 101. 103: Detectors in parallel according to any one of items 71 to 101. 104: Detectors in series and parallel according to any one of items 71 to 101. 105: A mid or far infrared detector comprising two or more metallic electrodes and pectin crosslinked by calcium ions, enabled by the change of the electric impedance at the said metallic electrodes enabled by the changes in the ionic conductivity of the said pectin with temperature. 106: An electrical mid or far infrared detector comprising a gel ionic conductor as a sensing element. 107: An electrical mid or far infrared detector comprising a gel comprising networks with covalent or ionic or physical crosslinks as a sensing element. 108: An electrical mid or far infrared detector comprising an hydrogel as a sensing element. 109: An electrical mid or far infrared detector comprising an aerogel as a sensing element. 110: An electrical mid or far infrared detector comprising pectin as a sensing element. 111: An electrical mid or far infrared detector comprising pectin crosslinked by calcium as a sensing element. 112: An electrical mid or far infrared detector comprising pectin crosslinked by metal ions as a sensing element. 113: An electrical mid or far infrared detector comprising pectin crosslinked by divalent ions as a sensing element. 114: An electrical mid or far infrared detector comprising pectin and calcium as a sensing element. 115: An electrical mid or far infrared detector comprising pectin and metal ions as a sensing element. 116: An electrical mid or far infrared detector comprising pectin and divalent ions as a sensing element. 117: An electrical mid or far infrared detector comprising hydrogel crosslinked by calcium as a sensing element. 118: An electrical mid or far infrared detector comprising hydrogel crosslinked by metal ions as a sensing element. 119: An electrical mid or far infrared detector comprising hydrogel crosslinked by divalent ions as a sensing element. 120: An electrical mid or far infrared detector comprising hydrogel and calcium as a sensing element. 121: An electrical mid or far infrared detector comprising hydrogel and metal ions as a sensing element. 122: An electrical mid or far infrared detector comprising hydrogel and divalent ions as a sensing element. 123: An electrical mid or far infrared detector comprising aerogel crosslinked by calcium as a sensing element. 124: An electrical mid or far infrared detector comprising aerogel crosslinked by metal ions as a sensing element. 125: An electrical mid or far infrared detector comprising aerogel crosslinked by divalent ions as a sensing element. 126: An electrical mid or far infrared detector comprising aerogel and calcium as a sensing element. 127: An electrical mid or far infrared detector comprising aerogel and metal ions as a sensing element. 128: An electrical mid or far infrared detector comprising aerogel and divalent ions as a sensing element. 129: An electrical mid or far infrared detector comprising gel crosslinked by calcium as a sensing element. 130: An electrical mid or far infrared detector comprising gel crosslinked by metal ions as a sensing element. 131: An electrical mid or far infrared detector comprising gel crosslinked by divalent ions as a sensing element. 132: An electrical mid or far infrared detector comprising gel and calcium as a sensing element. 133: An electrical mid or far infrared detector comprising gel and metal ions as a sensing element. 134: An electrical mid or far infrared detector comprising gel and divalent ions as a sensing element. 135: An electrical device comprising one or more of the sensing elements of items 36 to 64 and two or more electrodes. 136: An electrical device as said in item 65 wherein the said electrodes are made of a material selected from the group consisting of copper, silver, gold and aluminum. 137: An electrical series of sensors according to any one of items 36 to 66. 138: Sensors in parallel according to any one of items 36 to 66. 139: Sensors in series and parallel according to any one of items 36 to 66. 140: An electrical mid or far infrared detector comprising two or more metallic electrodes and pectin crosslinked by calcium ions, enabled by the change of the electric impedance at the said metallic electrodes enabled by the changes in the ionic conductivity of the said pectin with temperature. 141: A bolometer or microbolometer comprising a gel ionic conductor as a sensing element. 142: A bolometer or microbolometer comprising a gel comprising networks with covalent or ionic or physical crosslinks as a sensing element. 143: A bolometer or microbolometer comprising an hydrogel as a sensing element. 144: A bolometer or microbolometer comprising an aerogel as a sensing element. 145: A bolometer or microbolometer comprising pectin as a sensing element. 146: A bolometer or microbolometer comprising pectin crosslinked by calcium as a sensing element. 147: A bolometer or microbolometer comprising pectin crosslinked by metal ions as a sensing element. 148: A bolometer or microbolometer comprising pectin crosslinked by divalent ions as a sensing element. 149: A bolometer or microbolometer comprising pectin and calcium as a sensing element. 150: A bolometer or microbolometer comprising pectin and metal ions as a sensing element. 151: A bolometer or microbolometer comprising pectin and divalent ions as a sensing element. 152: A bolometer or microbolometer comprising hydrogel crosslinked by calcium as a sensing element. 153: A bolometer or microbolometer comprising hydrogel crosslinked by metal ions as a sensing element. 154: A bolometer or microbolometer comprising hydrogel crosslinked by divalent ions as a sensing element. 155: A bolometer or microbolometer comprising hydrogel and calcium as a sensing element. 156: A bolometer or microbolometer comprising hydrogel and metal ions as a sensing element. 157: A bolometer or microbolometer comprising hydrogel and divalent ions as a sensing element. 158: A bolometer or microbolometer comprising aerogel crosslinked by calcium as a sensing element. 159: A bolometer or microbolometer comprising aerogel crosslinked by metal ions as a sensing element. 160: A bolometer or microbolometer comprising aerogel crosslinked by divalent ions as a sensing element. 161: A bolometer or microbolometer comprising aerogel and calcium as a sensing element. 162: A bolometer or microbolometer comprising aerogel and metal ions as a sensing element. 163: A bolometer or microbolometer comprising aerogel and divalent ions as a sensing element. 164: A bolometer or microbolometer comprising gel crosslinked by calcium as a sensing element. 165: A bolometer or microbolometer comprising gel crosslinked by metal ions as a sensing element. 166: A bolometer or microbolometer comprising gel crosslinked by divalent ions as a sensing element. 167: A bolometer or microbolometer comprising gel and calcium as a sensing element. 168: A bolometer or microbolometer comprising gel and metal ions as a sensing element. 169: A bolometer or microbolometer comprising gel and divalent ions as a sensing element. 170: A device comprising one or more of the sensing elements of items 141 to 169 and two or more electrodes. 171: A device as said in item 170 wherein the said electrodes are made of a material selected from the group consisting of copper, silver, gold and aluminum. 172: A series of detectors according to any one of items 141 to 171. 173: Detectors in parallel according to any one of items 141 to 171. 174: Detectors in series and parallel according to any one of items 141 to 171. 175: A device comprising one or more elements or sensors or detectors described in any of the items 1 to 175 and a polyelectrolyte. 176: A device comprising one or more elements or sensors or detectors described in any of the items 1 to 175 and a polyelectrolyte gel.

Wherever alternatives for single separable features are laid out herein as "embodiments", it is to be understood that such alternatives may be combined freely to form discrete embodiments of the invention disclosed herein.

The invention is further illustrated by the following examples and Figures, from which additional embodiments and advantages can be drawn. These examples are meant to illustrate the invention but not to limit its scope.

Tab. 1 shows temperature response values from a measurement using a temperature sensor according to the invention.

Figure 17:
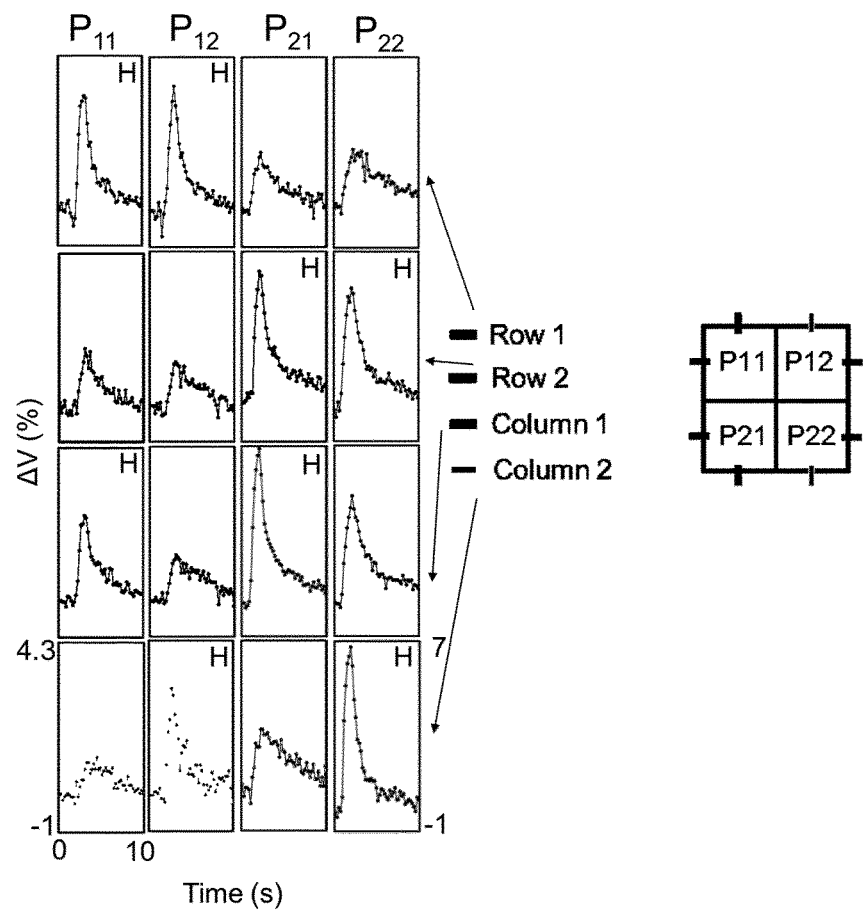
FIG. 17 shows the voltage (V) at the readout circuit for every row and column in a 4-pixel skin fabricated according to the present invention.

Tab. 2 shows the values representing the product of the signals in FIG. 17.

Tab. 3 shows the values reported in FIG. 12F. These values were obtained using the same procedure employed for Table 2.

DETAILED DESCRIPTION OF THE FIGURES

Figure 1:
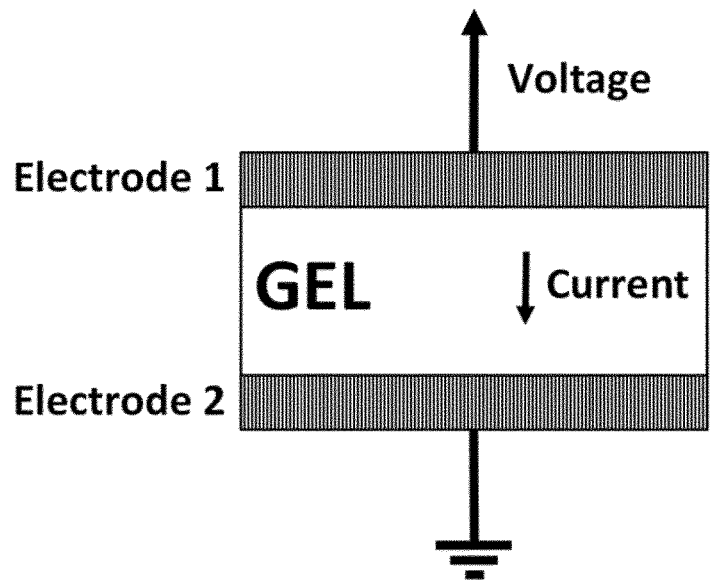
FIG. 1 shows a temperature sensor according to the present invention.

FIG. 1 shows a temperature sensor according to the present invention. The temperature sensor comprises an electrode 1, a gel, and an electrode 2, wherein the gel is positioned between the electrode 1 and the electrode 2.

Figure 2:
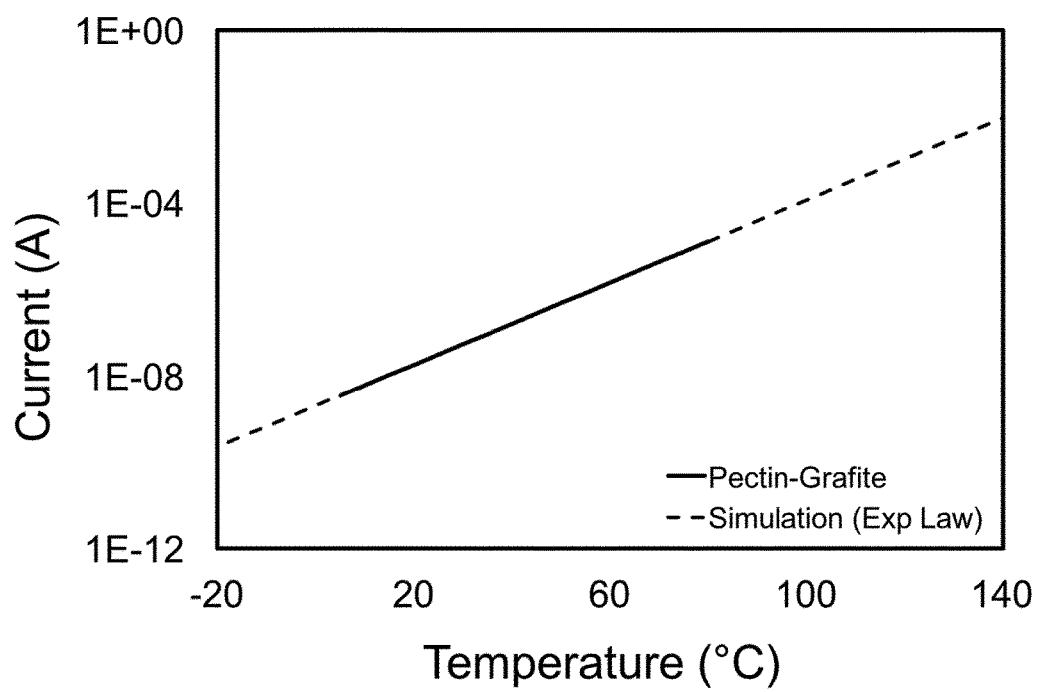
FIG. 2 shows the temperature-current characteristic of a pectin sensor containing graphite.

FIG. 2 shows a typical current (A) vs. temperature (° C.) plot derived from a measurement by means of a temperature sensor according to the present invention. Values depicted as a solid line have been measured on a temperature sensor, in which the sensor gel comprises graphite. Dotted lines represent simulations according to the activation energy of the gel sensor.

Figure 3:
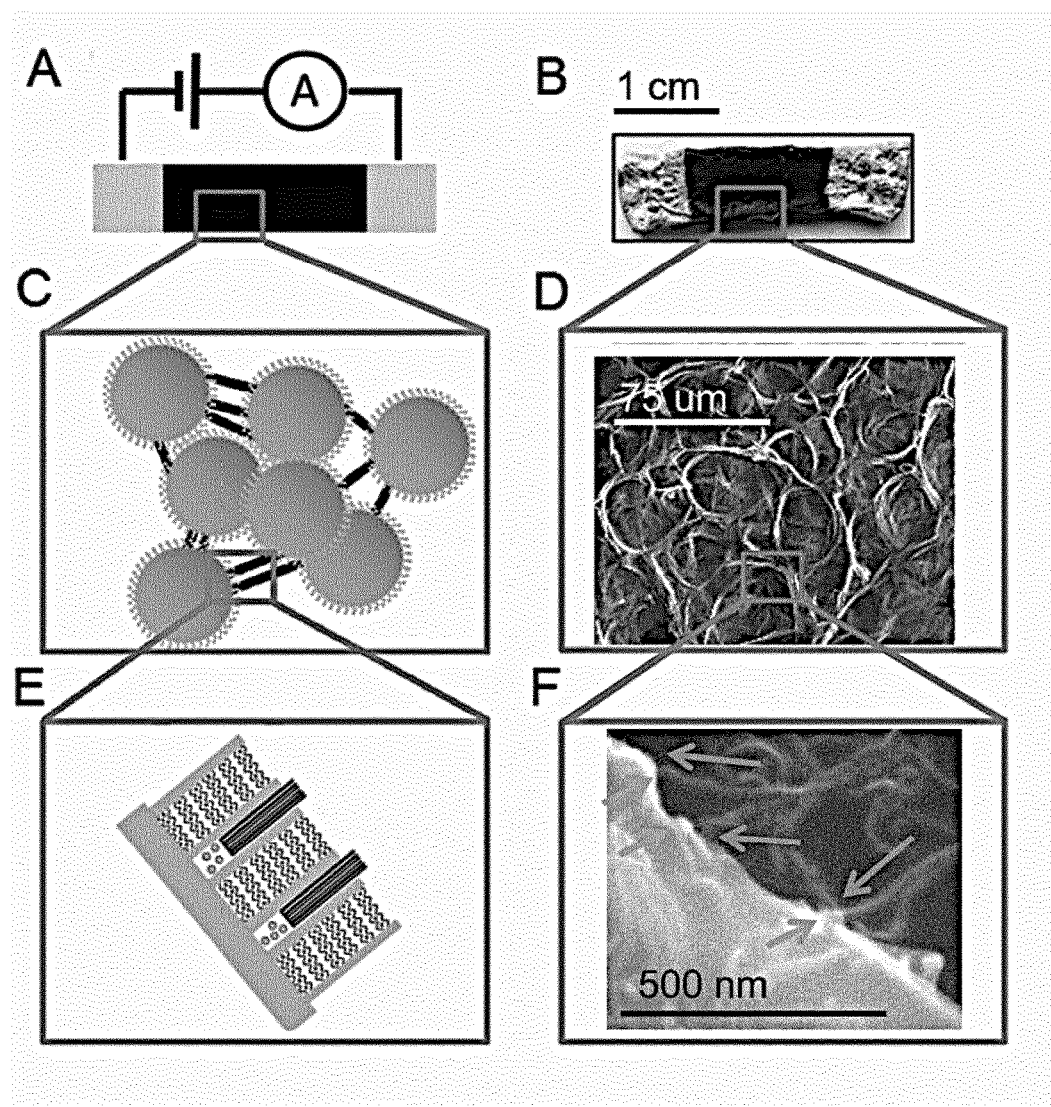
FIG. 3 shows schematic diagrams and scanning electron microscopy (SEM) images of cyberwood.

FIG. 3 shows schematic diagrams and scanning electron microscopy (SEM) images of cyberwood. (A) Representation of the material with sputtered co-planar gold electrodes and current measurement setup. (B) Optical image of a sample. (C) Diagram of BY-2 cells with MWCNTs. The cell walls are emphasized in grey. (D) SEM picture of tobacco cell (dark gray) with MWCNTs inside the cell wall (brighter lines). (E) Schematic diagram of the pectin backbone structure interconnecting cellulose microfibrils (grey bars) and the encapsulated metal ions in the egg-box structure. Micropores between cellulose microfibrils are shown filled with water and/or MWCNTs. (F) SEM image showing MWCNTs penetrating the cell wall of a BY-2 cell. The arrows indicate the edge of the cell wall and the MWCNTs.

Figure 4:
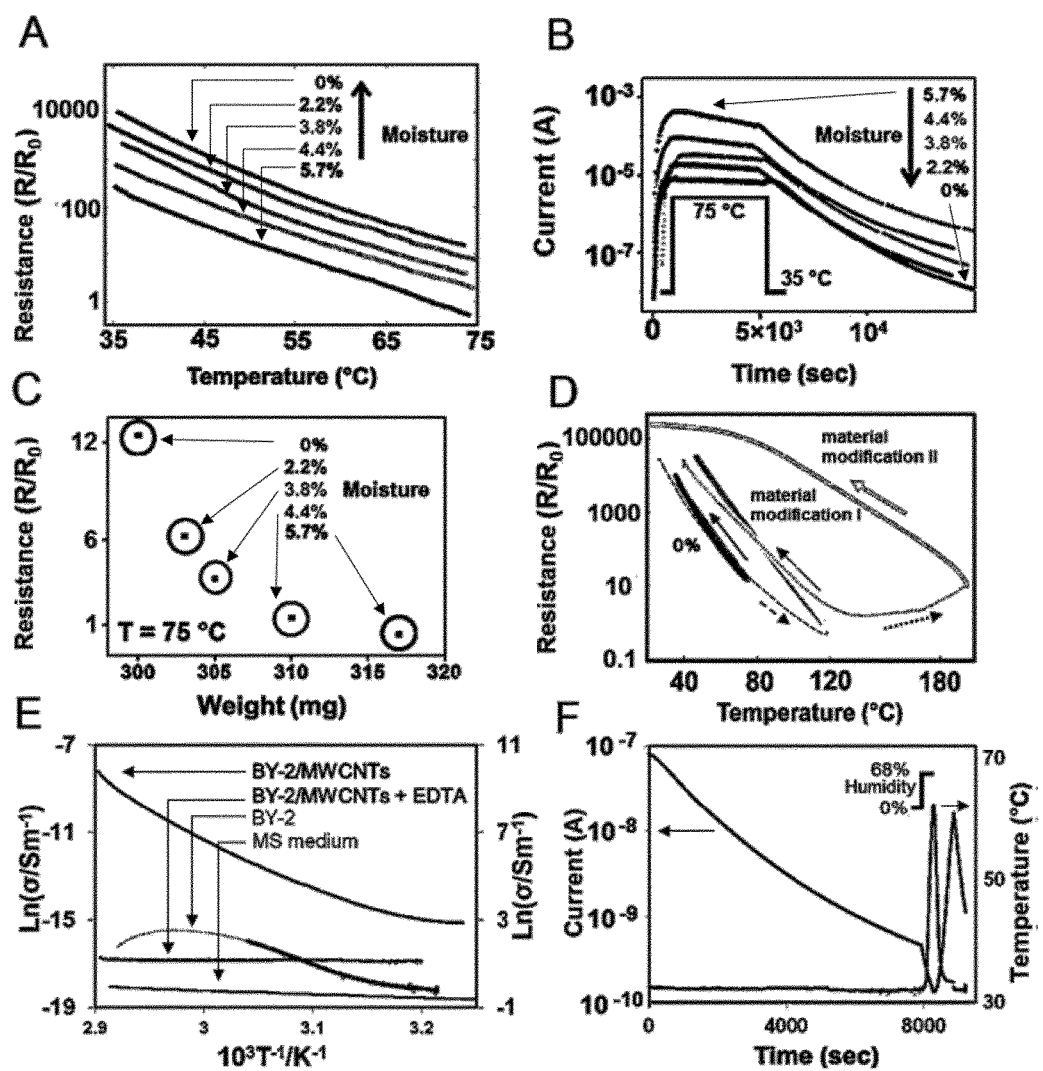
FIG. 4 shows the response of temperature and humidity sensors according to the present invention to temperature and moisture content variations.

FIG. 4. shows the response of cyberwood to temperature and moisture content variations. (A) Electrical resistance vs. temperature at different moisture contents: 5.7%, 4.4%, 3.8%, 2.2%, 0%. (B) Current vs. time during temperature cycles. Cycle I: 5.7% moisture content, Cycle II: 4.4% moisture content, Cycle III: 3.8% moisture content, Cycle IV: 2.2% moisture content, Cycle V: 0% moisture content. (C) Resistance vs. sample weight at 75° C. The weight loss corresponds to the moisture content: 5.7%, 4.4%, 3.8%, 2.2%, 0%. (D) Electrical resistance vs. temperature during cycles up to 200° C. 0% line: same measurement as in (A) at 0% moisture. The dashed line and arrow represent the sample cycling up to 120° C. Material modification line I line: cycle from 120 to 40° C. Dotted line: cycles up to 200° C. Material modification II line: cycle from 200 to 23° C. The open squares represent the sensitivity measured up to 75° C. The arrows indicate whether the measurement was performed during the heating or cooling part of the respective cycles. (E) Arrhenius plot of the conductivity of a cyberwood micro-sample; isolated BY-2 tobacco cells (black line values over 55° C. are dotted); cyberwood micro-sample with addition of EDTA and MS medium. (F) Temperature vs. time and current vs. time in a cyberwood micro-sample with addition of EDTA. The ambient relative humidity was suddenly increased at time (t=8000 sec).

Figure 5:
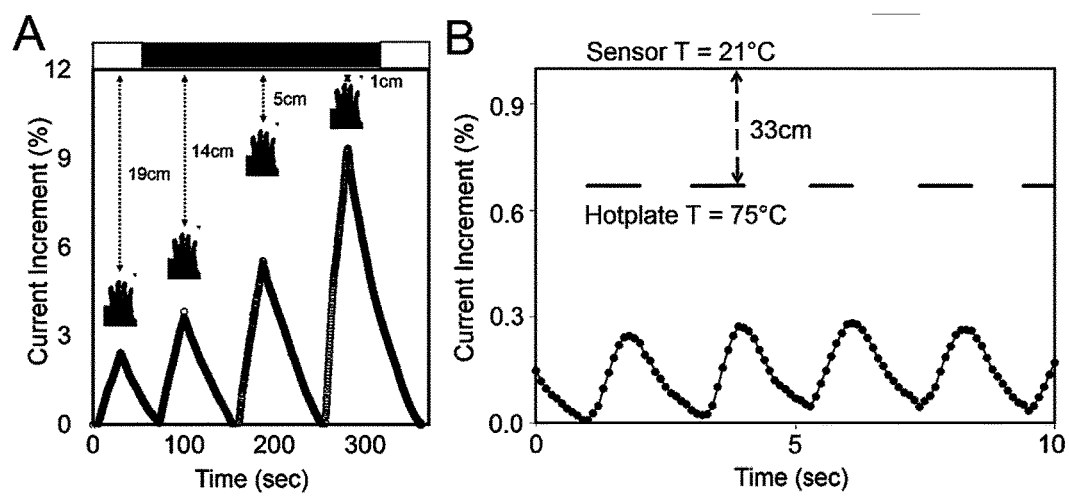
FIG. 5 shows data measured by a bolometer according to the present invention.

FIG. 5 shows an application of cyberwood as a thermal distance sensor. Plots show variations of the current in different cyberwood samples, as a function of the position, in and off axis, of heat emitting bodies in time. (A) Larger sample detecting the position of a hand. (B) Micro-sample detecting the position of a hotplate.

Figure 6:
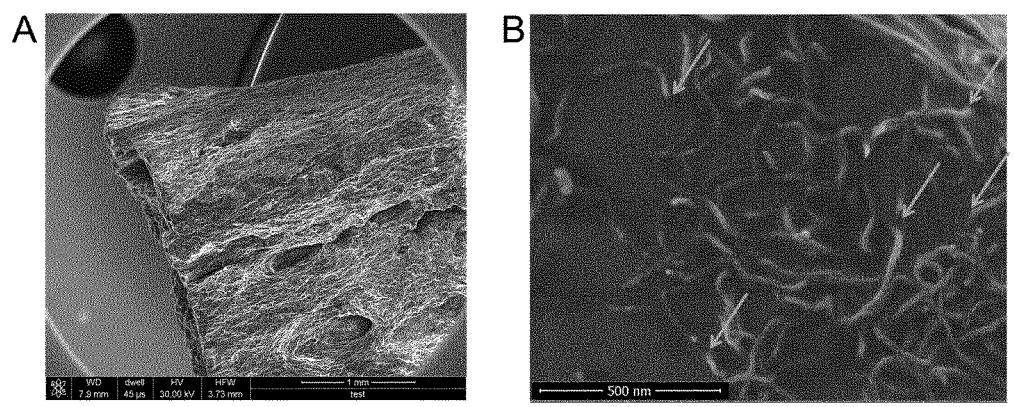
FIG. 6 shows scanning electron microscopy (SEM) images of cyberwood.

FIG. 6 (A) shows a low-magnification SEM picture of the cyberwood. FIG. 6 (B) shows a top view of a cell wall of BY-2 with MWCNTs on top. Arrows emphasize some penetration points.

Figure 7:
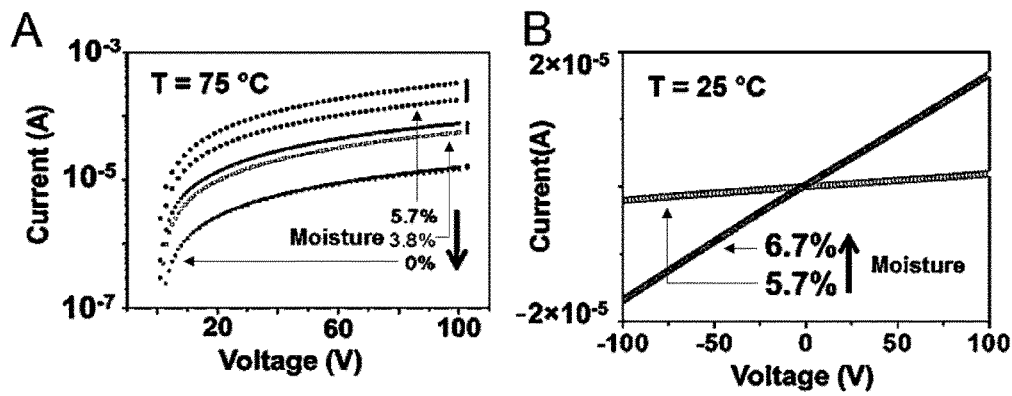
FIG. 7 shows current (A) vs. voltage (V) plots derived from measurements by means of temperature sensors according to the present invention.

FIG. 7 (A) shows the I-V characteristics at 75° C. of cyberwood for different final moisture contents: 5.7%, 3.8%, 0%, plotted in semi-log scale. The upper characteristic for each moisture content was measured immediately after the sample reached 75° C., while the lower curve was obtained after being kept for 100 min at 75° C. The 0% moisture content characteristics overlap, indicating that the dehydration at 75° C. is 0. The vertical bars on the right of the curves graphically represent the level of hydration of the sample. (B) I-V characteristic at 5.7% and 6.7% moisture content before cycling.

Figure 8:
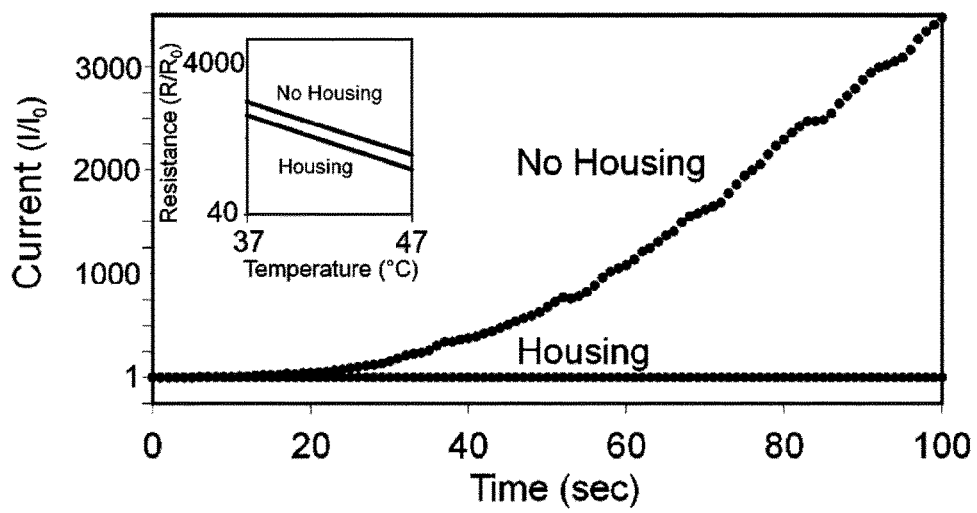
FIG. 8 shows a current (A) vs. time (s) plot derived from measurements by means of temperature sensors according to the present invention.

FIG. 8 shows current vs. time and resistance vs. temperature in a cyberwood sample with and without housing when ambient humidity is increased from 44% to 82%.

Figure 9:
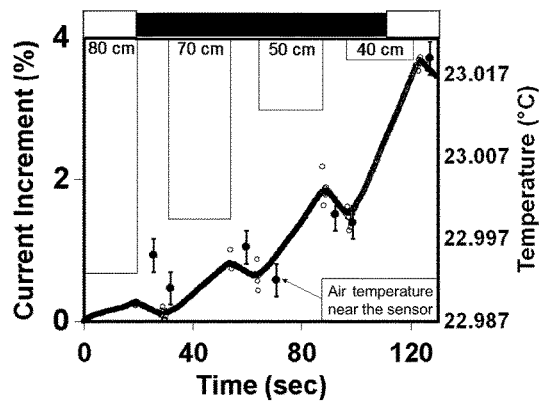
FIG. 9 shows data measured by a bolometer according to the present invention.

FIG. 9 shows cyberwood as a thermal distance sensor. The plot shows variations of the current measured across the sample as a function of the position of a heat-emitting body in time, detecting the position of a person moving in the room. The temperature of the air near the sensor was acquired via an independent measurement. The error bars correspond to the accuracy of the measurement system.

Figure 10:
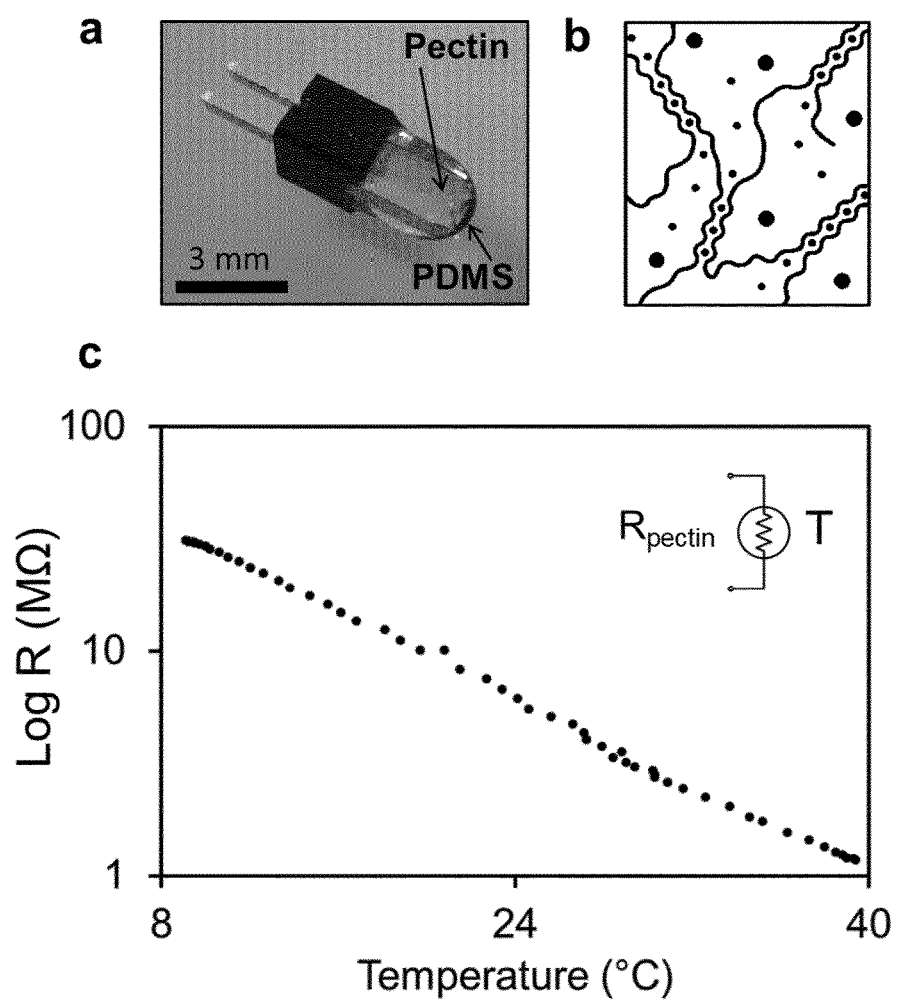
FIG. 10 shows a resistance (MΩ) vs. temperature (° C.) plot derived from measurements by means of a temperature sensor according to the present invention.

FIG. 10 shows a characterization of the pectin thermometer (A) Dehydrated pectin hydrogel enclosed in PDMS. (B) Model of the pectin network; solid lines: galacturonic acid; black circles: Calcium ions; black dots: water molecules. (C) Temperature responsivity of a dehydrated pectin thermometer. Inset: model of the thermistor.

Figure 11:
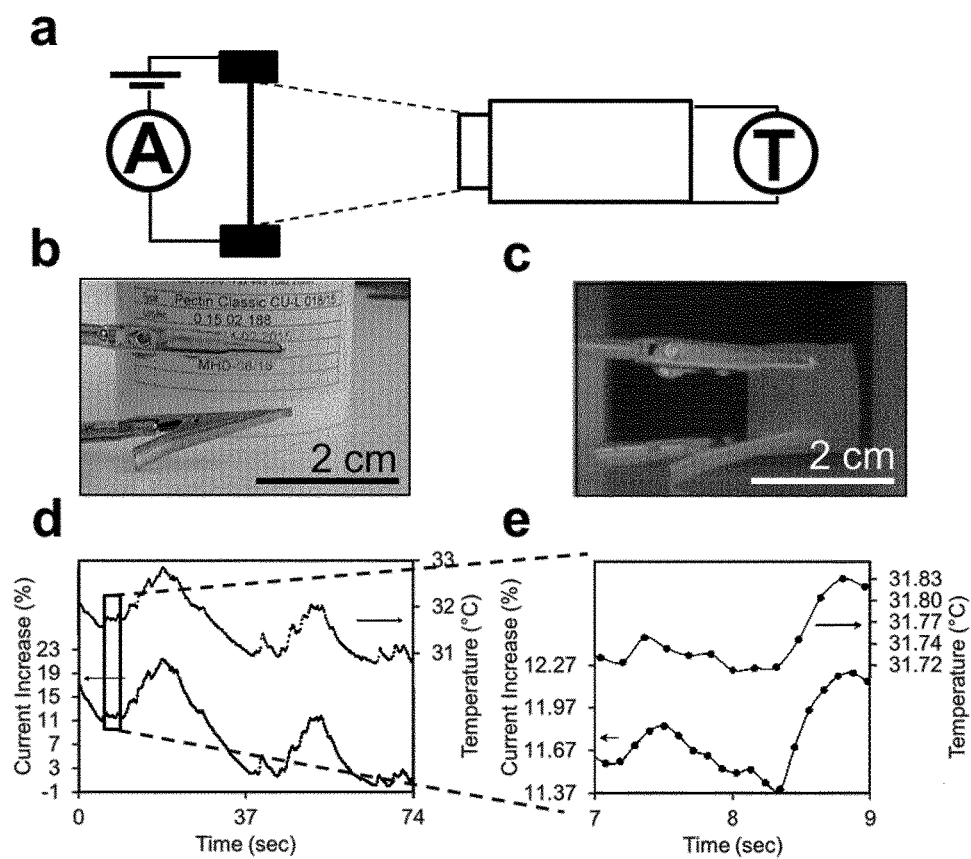
FIG. 11 shows a temperature sensor according to the present invention, current increase (%) vs. time (s) and temperature (° C.) vs. time (s) plots derived from measurements by means of the temperature sensor.

FIG. 11 shows a characterization of the pectin film (A) Measurement setup. A thermal camera acquires the temperature on the surface of a pectin film while two electrodes measure its current at a constant applied voltage. (B) Photograph of a pectin film. (C) Thermal-camera image of the pectin film in (A). (D) Current in the pectin film (left axis) vs. temperature on its surface (right axis). (E) Magnification of the black squared box measurements in (D); dots represent the measurement points.

Figure 12:
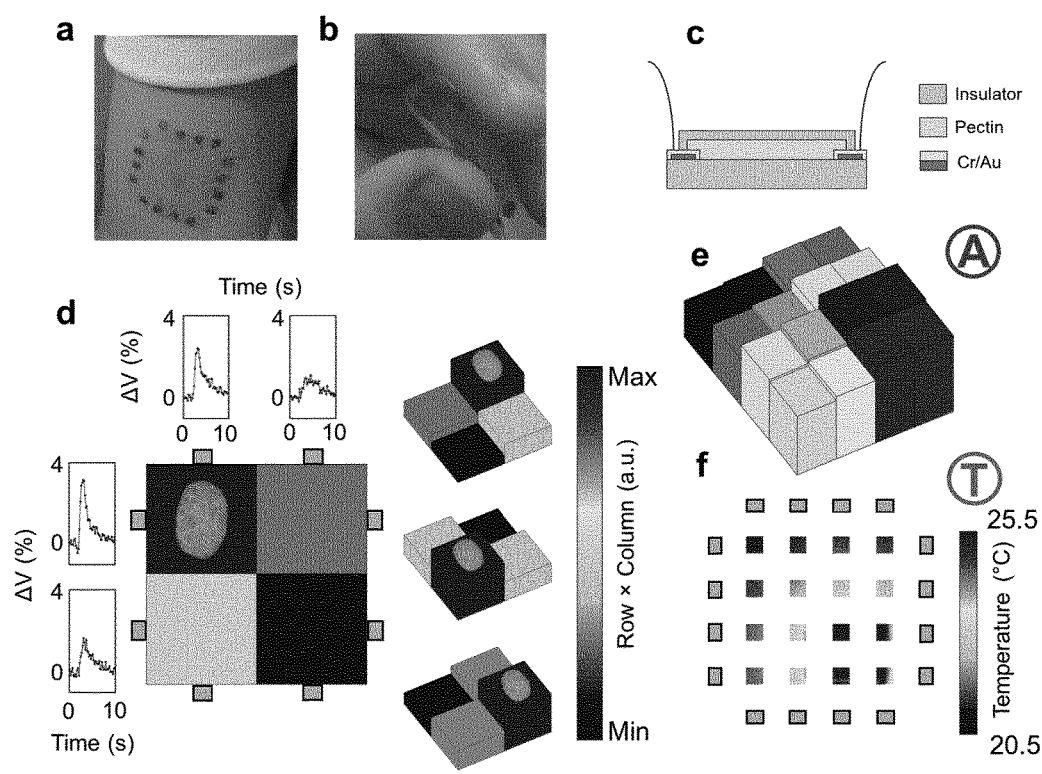
FIG. 12 shows a temperature sensor array according to the present invention, and measurement data generated by means of the temperature sensor array.

FIG. 12 shows the characterization of the temperature sensing skin. (A), (B) Pictures of a 16-pixel skin with PDMS insulator at the bottom and top of the pectin film. (C) Schematic of the skin. (D) Electrical response of a 4-pixel skin when a finger touched it in different positions. For the first pixel row and column signals at the readout circuit are shown. Greyscales represent values of row times column signals product (E) Electrical response of a 16-pixel skin when an object is placed at the bottom right corner. (F) Pixelated thermal image of the object producing the electrical response reported in (E).

Figure 13:
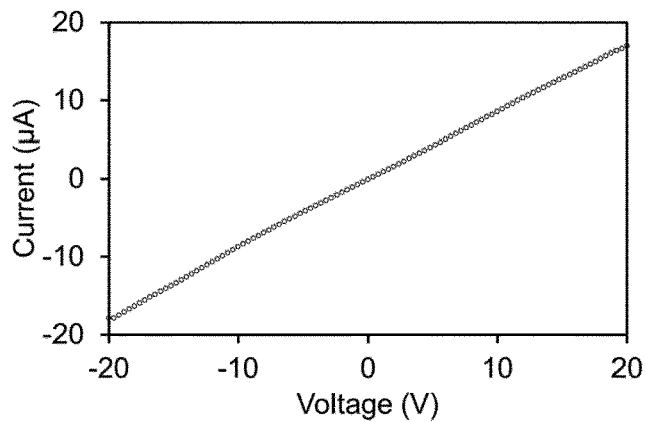
FIG. 13 shows a voltage (V)-current (A) characteristic of a pectin gel sensor according to the present invention.

FIG. 13 shows the current voltage characteristic of a pectin thermistor. Circles: measurements.

Figure 14:
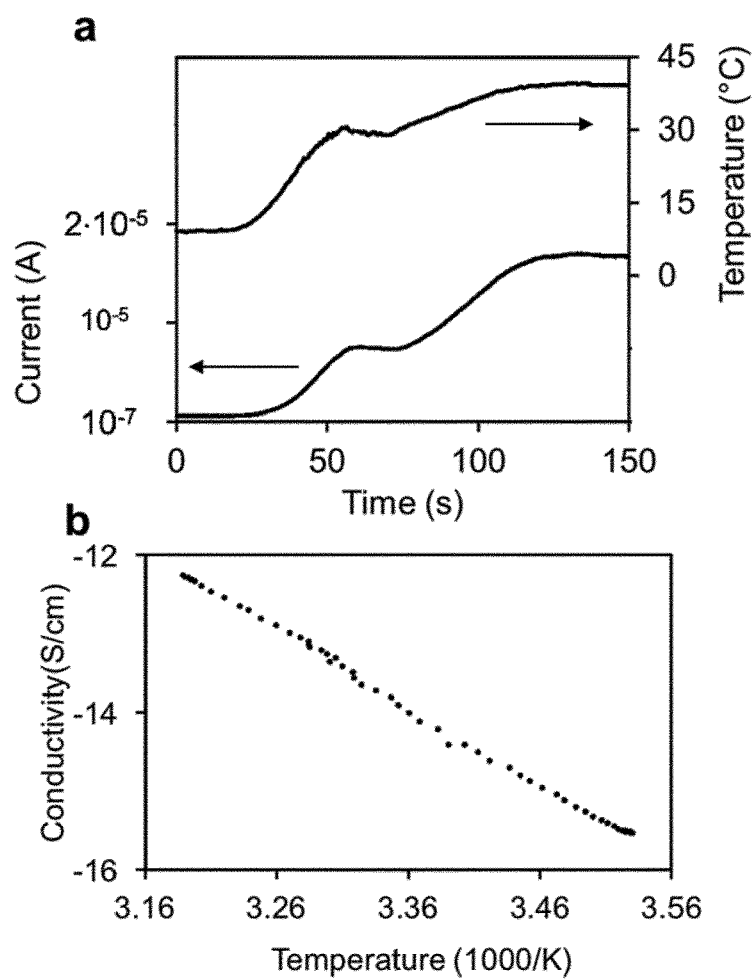
FIG. 14 shows temperature (° C.) and current (A) on a pectin gel sensor fabricated accordingly to the present invention and the Arrhenius plot of its electrical conductivity.

FIG. 14 shows (A) Temperature and current on a pectin thermistor as a function of time. Left axis: current on the thermistor. Right axis: temperature in the thermistor. (B) Arrhenius plot of electrical conductivity derived from FIG. 14A.

Figure 15:
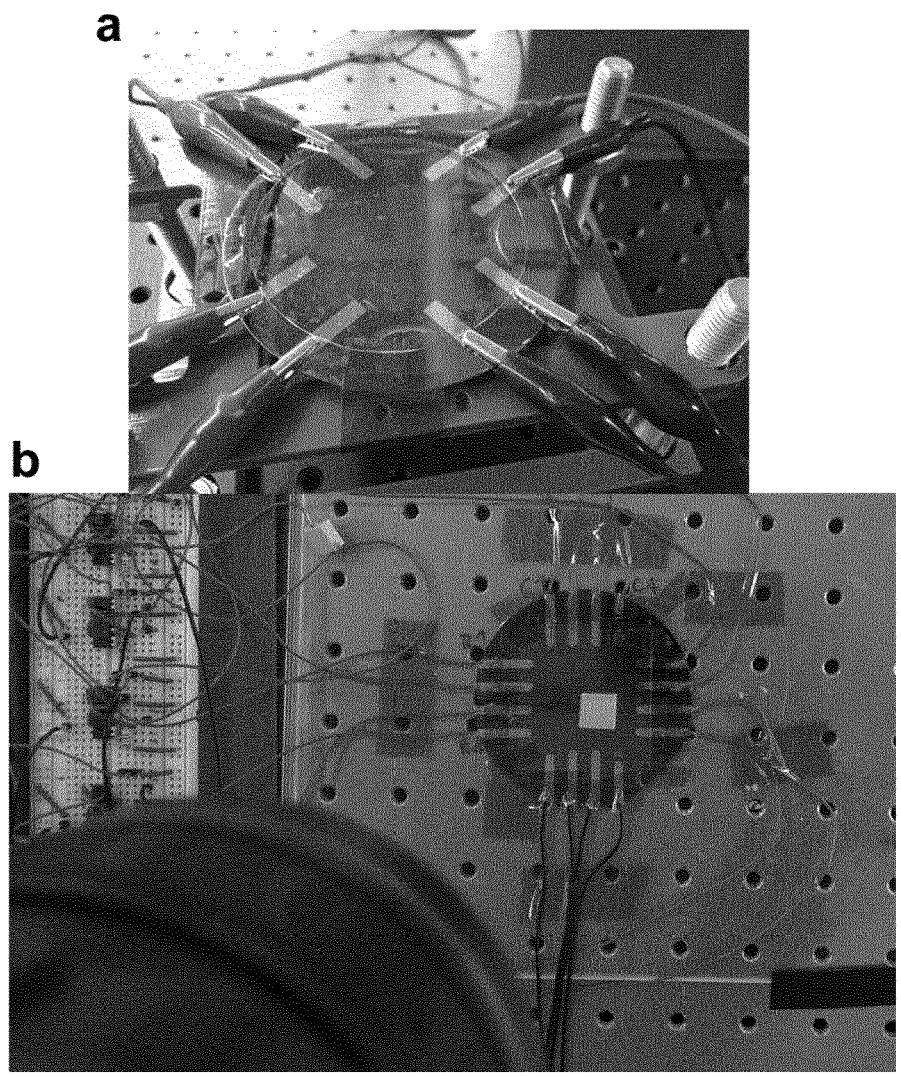
FIG. 15 shows the setups for the electrical measurements on the sensitive skin fabricated according to the present invention.

FIG. 15 shows the setup for the electrical measurements on the sensitive skin. (A) A 4-pixel skin. (B) A 16-pixel skin.

Figure 16:
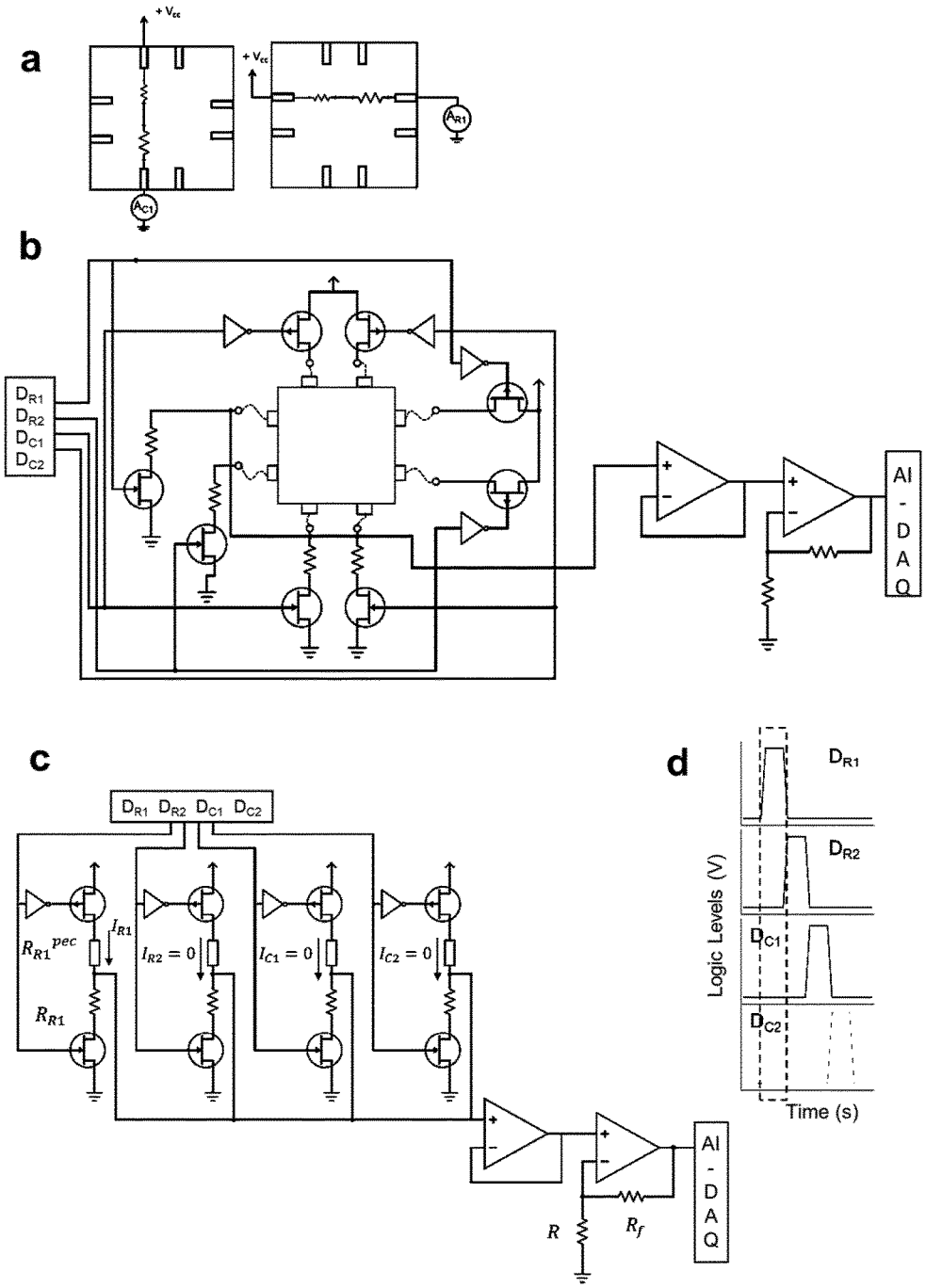
FIG. 16 shows the read-out circuit for a 4-pixel skin fabricated according to the present invention.

FIG. 16 shows the read out circuit for the 4-pixel skin. (A) Working principle. (B), (C) Electrical schematic of the read out circuit. (D) Enabling signals.

FIG. 17 shows the voltage at the readout circuit for every row and column in a 4-pixel skin. All the time scales are between 0 and 10 sec. All the amplitudes are between −1 and 4.3 except $P_{22}$ column 2, which is between −1 and 7. Signals aligned in vertical have been taken synchronously.

Figure 18:
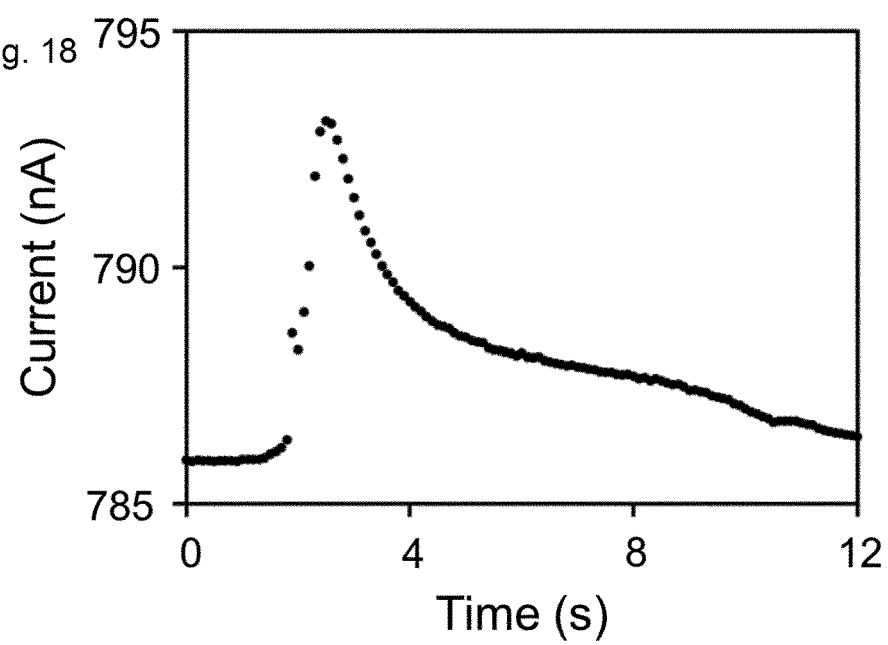
FIG. 18 shows current (A) vs. time (s) when a film fabricated according to the present invention is touched with a finger.

FIG. 18 shows current vs. time when the film is touched with a finger. Black dots: Current measurements.

Figure 19:
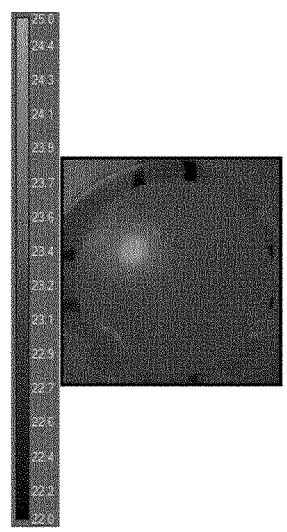
FIG. 19 shows the thermal image of a skin fabricated according to the present invention just after touched with a finger.

FIG. 19 shows the thermal image of the skin just after being touched with a finger.

Figure 20:
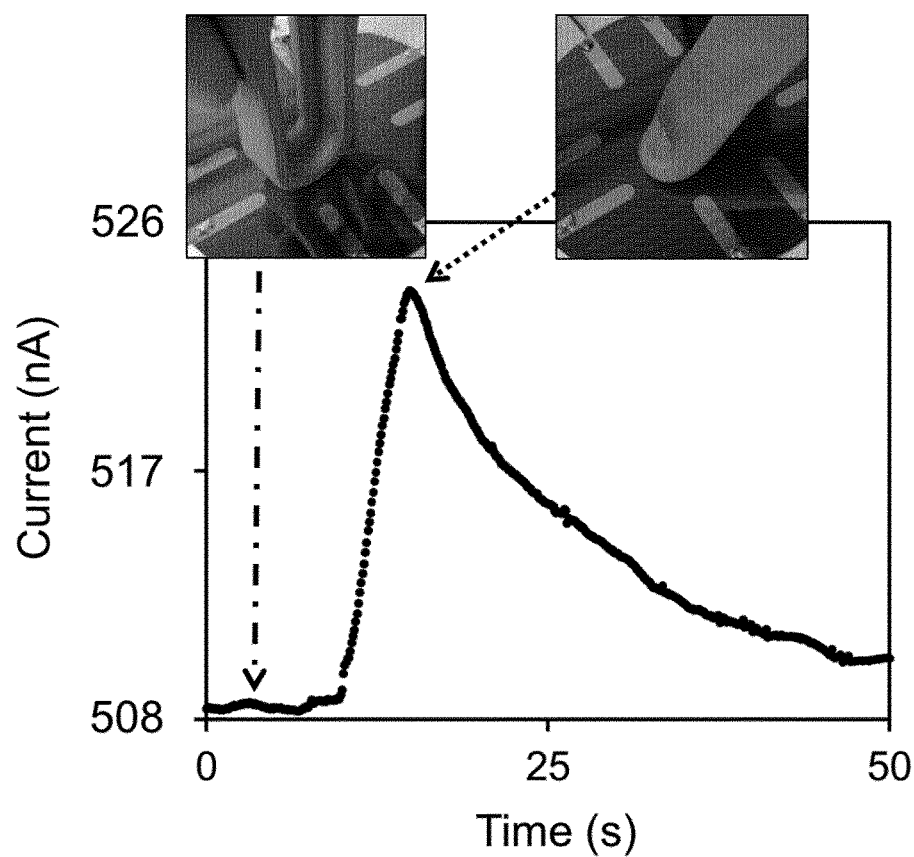
FIG. 20 shows the sensitivity to the touch of a finger on a 4-pixel skin fabricated according to the present invention.

FIG. 20 shows the sensitivity to the touch of a finger on a 4-pixel skin.

Figure 21:
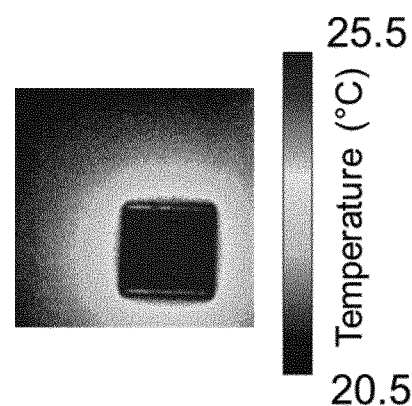
FIG. 21 shows an aluminum square in contact with the 16-pixel skin fabricated according to the present invention.

FIG. 21 shows an aluminium square in contact with the 16-pixel skin.

Figure 22:
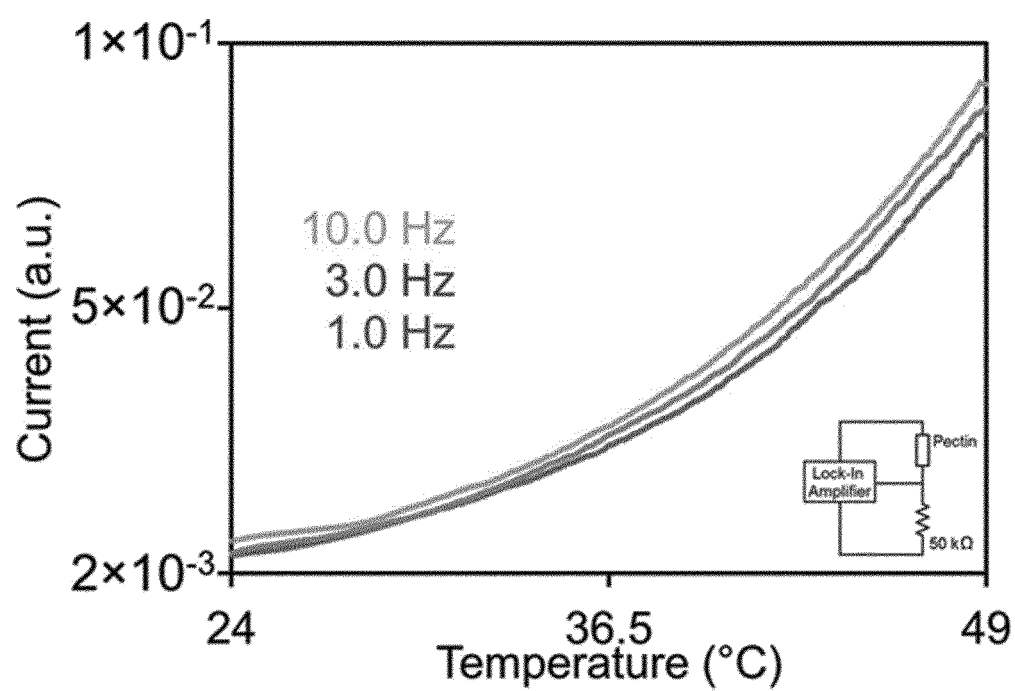
FIG. 22 shows AC measurements on the pectin films.

FIG. 22 shows a typical thermal response measured at three different frequencies on the small pectin film samples shown in FIG. 10a. The current is reported in arbitrary units since it was measured as the RMS value of the voltage drop on a resistor (50 kΩ) in series with the sample (see inset of FIG. 22).

Figure 23:
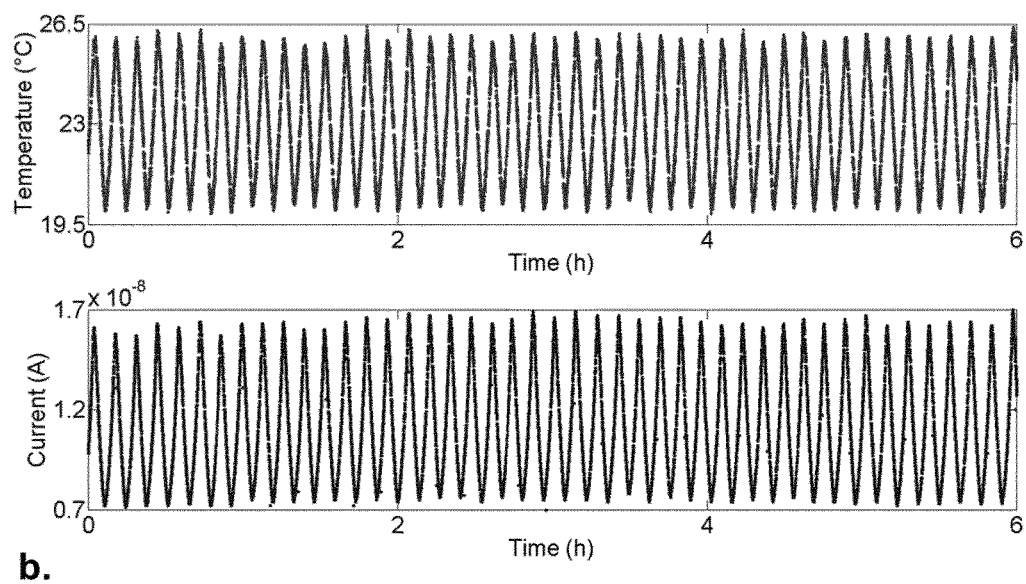
FIG. 23 shows thermal cycles on the pectin films.
Figure 23:
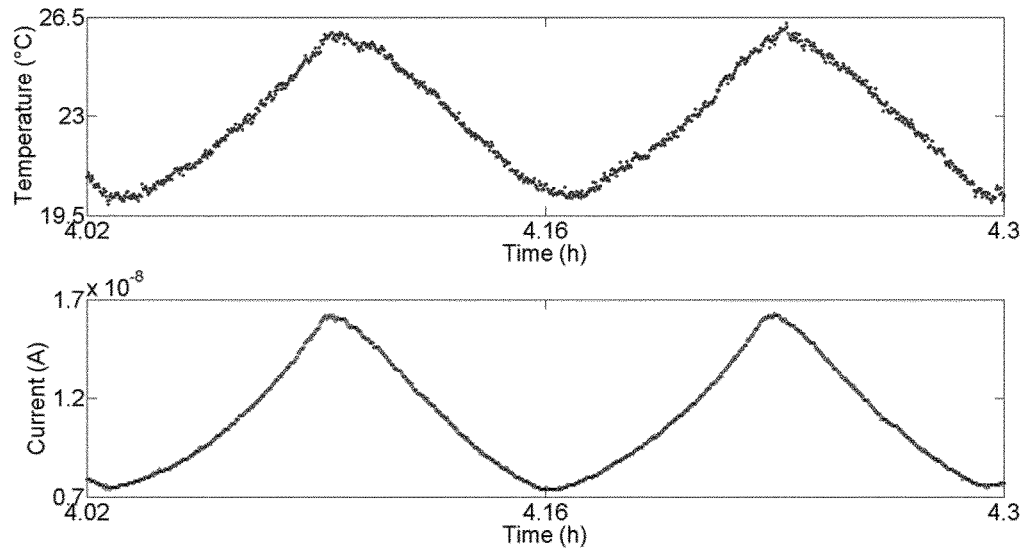

FIG. 23 shows a typical current in a pectin film sample when the temperature is cycled for 6 h between 20 and 26° C. The material responds stably and the responsivity matches with FIG. 10c. FIG. 23b shows a 2-cycle zoom.

Tab. 1 shows the calculation of an effective TCR coefficient $(\Delta R/R)/(\Delta T)$ from experimental data in FIG. 4A. Note that the TCR values are calculated over a 40° C. temperature interval (i.e., between the maximum and minimum temperatures in the experiments shown in FIG. 4A).

Tab. 2 shows the values representing the product of the signals in FIG. 17. For each of the 4 positions of the finger ($P_{11}$, $P_{12}$, $P_{21}$, $P_{22}$), the maximum in the variation of the voltage for each row and column ($R_1$, $R_2$, $C_1$, $C_2$) is taken. Values are multiplied as follows: $R_1C_1$, $R_1C_2$, $R_2C_1$, $R_2C_2$, and the results are normalized for each experiment.

Tab. 3 shows the values reported in FIG. 12F. These values were obtained using the same procedure employed for Tab. 2.

Materials and Methods

For the experiments described in Example 1, a 1% sodium dodecyl sulfate (SDS) solution was prepared in MilliQ water and MWCNTs were added. The solution was left to rest for 150 min. To reduce the clusters in the solution the suspension was then sonicated at room temperature for 20 min. Following, additional purification steps were performed: after sonication, the supernatant was collected and allowed to precipitate for 18 h in a new container. The supernatant was collected again, centrifuged at 10,000 rpm for 5 min at room temperature, and the final supernatant was used for experiments. This solution was added to a suspension of growing tobacco BY-2 cells (Di Giacomo et al. (2013), *IEEE Trans NanoTechnol* 12(6):1026-1030). Five independent cells/MWCNTs samples were produced and each analyzed individually. Commercially available CNTs (non-modified type "3100" MWCNTs, Nanocyl®) were used in the solution with SDS. The BY-2 cell line was derived from the callus of seedlings of *Nicotiana tabacum* and propagated in modified MS medium supplemented with 3% sucrose, 600 μg/ml $KH_2PO_4$, 0.2 μg/ml 2,4-dichlorophenoxacetic acid (2,4-D), and 30 μg/ml thiamine-HCl. Cells were grown in large flasks on a rotary shaker at 130 rotations/min at 25° C. in the dark. 10% of stationary phase cells were transferred to a fresh medium every week. Spontaneous aggregation of cells was observed with tobacco cells combined with MWCNTs. After 24 hours a gel-like material formed, was collected and dried at 47° C. for 15 days. Macroscopic samples were fabricated ca. 2 cm long, ca. 1 cm wide, and ca. 3 mm thick and microscopic samples 500 μm long, 3 mm wide, and 50 μm thick. Control samples of BY-2 cells only were produced by depositing and compacting a single layer of BY-2 cells on a substrate. The control samples had the same dimensions as the microscopic samples.

Scanning electron microscopy (SEM) images were obtained using a field emission gun-scanning electron microscope (FEG-SEM) model Inspect F, FEI Company, equipped with an Everhardt-Thornley secondary electron detector (SED). FIG. 6 shows the microstructure of cyberwood at low magnification.

All electrical measurements were performed in a two-point contact geometry using Keithley model "2400" and Keithley model "2635" source measurement units. Three different biases in the different experiments were applied: 100 V, 20 V and 10 V. The choice of the applied bias was based on the size of the samples tested and the temperature range of the experiments. No variation in the material electrical response was recorded as a function of applied voltage. This is due to the fact that the I-V characteristics of the material, reported in FIGS. 7A and 7B, are linear. The experiments described in FIGS. 4A,B,C were performed at 100 V while that of FIG. 4D, FIG. 5A and FIG. 8 and FIG. 9 were performed at 20 V. The experiments described in FIG. 4E,F and FIG. 5B were performed at 10 V.

To measure temperature a Fluke 1502A thermometer was used in combination with a 5627A platinum resistance thermometer probe. A Heratherm advanced protocol oven with a capacity of 60 L was used to perform temperature cycles. The electrical power dissipated in the samples during all tests was very low (hundreds of μW), as such the samples' self-heating was negligible.

For the experiments described in Example 2, a commercially available citrus low-methoxylated pectin (LMP) with a degree of methylation of 34% and a content of galacturonic acid of 84% (Herbstreith&Fox©) was used to produce the material. The pectin powder (2% w/vol) was dissolved at 60° C. in ultrapure water, and stirred at 1,000 rpm to obtain a uniform solution at pH 6. To obtain the thermometers $CaCl_2$ powder was added to reach 32 mM (corresponding to a stoichiometric ratio $R=[Ca^{2+}]/2[COO^-]$ of 1). To obtain films and skins the pectin solution was poured onto substrates and then immersed into a 32 mM $CaCl_2$ solution. After gelation the highly hydrated skins and films were transferred to a vacuum chamber and dehydrated at 12 mbar overnight. The final water content in the hydrogel was 30%.

A voltage of 18V was applied to the skin rows and columns. Electrical measurements in FIG. 10C, 11D, 11E, were performed in a two-point contact geometry using Keithley model 2635 source measurement units. Electrical measurements in FIG. 12 were obtained with the readout circuit and a DAQ National Instruments BNC-2110.

Example 1

Here, the exceptionally high temperature- and moisture-sensitivity of a biological cells-CNT composite is described and the mechanisms of temperature sensitivity governing these responses are detailed and validated.

Characterization

The microstructure of the produced material resembles that of natural wood (see FIG. 6). The presence of MWCNTs confers structural stability and a high electrical conductivity, which can be exploited to connect the samples to an external circuit. Hence, the material was termed cyberwood. The method used to synthesize this material is very inexpensive and scalable. Two sets of samples were produced and tested at different scales varying in volume by about four orders of magnitude (see Materials & Methods). The use of these materials is demonstrated as scalable thermal sensors and the fundamental mechanisms governing their response are described.

To measure the electrical properties of the larger (macroscale) samples co-planar gold electrodes were sputtered at their extremities (FIGS. 3A and 3B), and to measure the smaller (microscale) samples, they were deposited on gold electrodes on a substrate. Measurements were also performed with steel contacts and no significant difference was found. Scanning electron microscopy images of the samples show that MWCNTs penetrate partially the cell wall and form a complex network among cells (FIGS. 3C and 3D). A schematic diagram of the MWCNTs/cell wall nano-structure, comprising the pectin backbone (Sriamornsak P (2003), *IEEE Trans NanoTechnol* 12(2):111-114) is shown in FIG. 3E.

CNT and Cell Wall Penetration.

Studies on toxicity of MWCNTs on isolated plant cells (Tan et al. (2009), *Carbon* 47(15):3479-3487) reported TEM images in which MWCNTs were seen to localize only within the cell wall and not intracellularly, implying interaction with the cell wall. These authors concluded that such a phenomenon is due to physical wrapping that allows the MWCNTs to penetrate into the space among the residues of the polysaccharides cellulose and pectins. Other mechanisms not implying physical penetration but adhesion forces would require functionalized MWCNTs that are not used in the present study. For example, Li et al. reported several chemical bonding and electrostatic forces between Ox-MWCNTs and polypeptides that they proved depend specifically on the MWCNTs oxidation (Li et al. (2006) *J Phys Chem B* 110(25):12621-12625). As in Tan et al. (2009), *Carbon* 47(15):3479-3487, the MWCNTs used for our study are pristine and not functionalized implying that the physical wrapping is the dominant phenomenon inside the cell wall structure. This was confirmed by our previous results (Di Giacomo et al. (2013) *IEEE Trans NanoTechnol* 12(2):111-114) on *C. albicans* and also by FIG. 3F and FIG. 6 SEM images on BY-2 cells.

Resistance of the larger samples was monitored as a function of temperature at different values of moisture content following different thermal cycles (see FIG. 4A). Samples were subjected to slow temperature variations, between 35 and 75° C., to control the sample's moisture content. All measurements, performed at thermal equilibrium, showed that resistance decreased with increasing temperature. The measured resistance decreased by almost three orders of magnitudes in a 40° C. temperature increase. This value corresponds to an effective TCR of $-1,730\%$ $K^{-1}$ (see Table 1). To determine the stability of the material over a long period of time the variation of the current as a function of time at constant temperature was measured (FIG. 4B). In these tests the temperature of samples with different moisture contents was rapidly ramped from 35 to 75° C. and the temperature was held constant at 75° C. for ca. 100 min before cooling. Samples with increasingly higher moisture content showed a decrease of the measured current at constant temperature indicating they were drying. Since the sample measured at 75° C. at 0% moisture showed no change in the current with time, it was assumed that it could not have been dried further at this temperature (see also additional experiments reported in FIG. 7A and its discussion). The process of dehydration is reversible (FIG. 7B).

To quantify the effect of the moisture content on the samples' electrical response, the variation of the sample's electrical resistance as a function of the sample's weight was measured (indicating different water content, FIG. 4C). These results suggest that cyberwood can be used as a humidity sensor as long as temperature is kept constant. The same material can be used as a temperature sensor, as long as humidity is kept constant. To show that it is possible to discriminate between the temperature contribution and that of the moisture of the environment, without monitoring the sample's weight, the material was encased in a polymeric housing (FIG. 8). The presence of the housing did not change the measured temperature response (see inset in FIG. 8).

The optimal performance of cyberwood was found below 100° C. Above this temperature, the properties of the cellular material decrease. To identify the maximum operating temperature of the material the electrical resistance was measured cycling the samples at increasing temperatures up to 200° C. (FIG. 4D). Measurements revealed an unchanged sensitivity from 25° C. up to ca. 100° C., above which irreversible modifications of the cellular matrix occurred. When the sample was heated up to 120° C. (dotted line) and then slowly cooled to 40° C. its colour changed from black to brown that suggests that structural changes had occurred. To emphasize the change in slope of the curves two parallel lines (squares) were drawn representing the responsivity measured up to 75° C. When the sample was heated up to 200° C. the material changed further its electrical temperature behaviour. This was expected since, in simulations reported earlier, cellulose changes its molecular structure at similar temperatures (Matthews et al. (2011), *J Phys Chem B* 115(10:2155-2166). During this higher temperature cycle the sample's colour changed to dark woody-brown tone and its weight reduced considerably and irreversibly. Nevertheless, the resistance-temperature response spanned almost four orders of magnitudes (FIG. 4D).

Sensing Mechanisms.

Experiments were performed to understand the mechanisms contributing to the extreme temperature and humidity sensitivity of the cyberwood. Mixed ionic and electronic conductivities were expected and tests were designed to deconvolve the contribution of each mode. FIG. 4E shows the Arrhenius plots of the conductivity of a cyberwood micro-sample (BY-2/MWCNTs) and that of control experiments. No variation was found in the micro-sample temperature response compared to larger samples. Measurements on samples obtained with isolated tobacco cells in the absence of MWCNTs (BY-2, black line) also presented high temperature responsivity, though this phenomenon was transient. Since BY-2 samples required high water content for being conductive they became unstable at temperatures above 55° C. (black dotted line) due to water loss. In addition, even at low temperatures, their lifetime was limited to a few cycles, due to cell degeneration and loss of structural stability. Cyberwood samples tested over a 12-month period did not show any change in their thermal or mechanical response. These experiments proved that the cyberwood's sensitivity to temperature is primarily due to the structure of plant cells.

The temperature sensitivity of plants is due to the presence of ions in the cell wall (Fensom (1966) *Can J Plant Sci* 46(2):169-175). The egg-box structure of pectin inside the plants' cell wall contains metal ions such as $Ca^{2+}$ (Sriamornsak P (2003), *IEEE Trans NanoTechnol* 12(2):111-114), FIG. 3E. These ions are responsible for the cross linking between pectin chains, and this process is disfavoured as temperature increases (Cardoso et al. (2003), *Food Hydrocoll* 17(6):801-807). As a consequence, the number of free ions available for conduction increases with temperatures. To investigate the role of $Ca^{2+}$ ions, micro-samples treated with 15 μL of 0.5 M EDTA (ethylenediaminetetraacetic acid), a chelating agent for divalent ions, were measured (FIG. 4E). The addition of EDTA eliminated the temperature sensitivity of the material proving the central role of pectin-$Ca^{2+}$. The conductivity increment due to the presence of MWCNTs is constant in temperature (FIG. 4E,), while the number of free $Ca^{2+}$ ions available for current transport increases exponentially with temperature. The presence of MWCNTs provides a permanent conductive pathway, and substitutes water when the material is completely dehydrated. Therefore, MWCNTs are responsible for raising the background conductivity and stabilizing the electrical response, while the number of $Ca^{2+}$ ions available for conduction is responsible for the current increase with temperature.

The sample's sensitivity to humidity was still present after adding EDTA (FIG. 4F). For the results reported in FIG. 4F, the sample was tested at low, constant relative humidity, while changing the temperature (monitored with an independent thermometer). After ~2 h (~8,000 s) the humidity of the environment was suddenly increased to 68% and subsequently decreased. The measured current increased sharply and then decreased, following humidity and independently of the temperature. This demonstrates that the sensitivity of cyberwood to humidity is not related to the presence of divalent $Ca^{2+}$ ions and can be decoupled from the temperature response.

The cyberwood's conductivity increases ~25 times when the internal moisture content is increased between 0 and 5.7% at 75° C. A comparable behaviour has been described for microcrystalline cellulose (MCC) and has been attributed to protons jumping between neighbouring water molecules bound to cellulose $OH^-$ groups on the amorphous microfibril surfaces (Nilsson et al. (2006), *J Phys Chem B* 110(32): 15776-15781; Nilsson et al. (2003), *Chem Phys* 295(2):159-165; Nilsson et al. (2006), *J Phys Chem B* 110(41):20502-20506). Cyberwood presents similar density (1.03 g/cm³) to MCC (Nilsson et al. (2006), *J Phys Chem B* 110(32):15776-15781; Nilsson et al. (2003), *Chem Phys* 295(2):159-165; Nilsson et al. (2006), *J Phys Chem B* 110(41):20502-20506). In addition, the cyberwood fractal dimension, measured using impedance spectroscopy (Di Giacomo et al. (2013), *IEEE Trans NanoTechnol* 12(6):1026-1030), is D=2.4 and is in line to values reported for MCC in (Nilsson et al. (2006), *J Phys Chem B* 110(32):15776-15781). The concomitant presence of these two parameters indicates the presence of micropores, which have dimensions between 5-35 nm in size. The magnitude of the water-induced proton conductivity, at given moisture content, is determined by the connectivity of the micropores (Nilsson et al. (2006), *J Phys Chem B* 110(41):20502-20506). At densities between ca. 0.7 and 1.2 g/cm³ the pore networks were shown to percolate, facilitating the charge transport through the MCC compact (Nilsson et al. (2006), *J Phys Chem B* 110(41):20502-20506). The same mechanism is supposed to occur in cyberwood.

To compare the cyberwood's response to that of an electrolyte with the same ionic strength as that present in plant cells, we tested the temperature sensitivity of Murashige and Skoog growth medium only (MS), as shown in FIG. 4E. It is evident that the TCR of the MS medium is rather small. Temperature response of cyberwood is also ~300 times higher than the best electrolyte materials either solid, liquid, gel, organic or polymeric (Kamaya et al. (2014), *Nat Mater* 13(4):400-408).

Temperature at Distance

The very high responsivity to temperature changes of cyberwood suggests that it can be used as temperature distance sensor. The distance of a warm body at fixed temperature can be inferred by the temperature measurements at constant environmental temperature (see FIG. 9). FIG. 5 shows the capacity to detect the presence of bodies irradiating heat (e.g., a hand and a hotplate) positioned at different distances from the sensor. We tested two cyberwood samples (a larger one and a smaller one) placed in an open oven at 23° C., at constant relative humidity. We first measured the variation of current across the larger sample in response to the motion of a hand positioned in four different locations, ranging from 1 to 19 cm away from the sample (FIG. 5A). At each position, the hand was held still for 30 s and then rapidly moved away. In correspondence to each hand movement, the current measured across the sample ramped to a different value and then decreased to a reference value corresponding to a temperature of 23° C. A similar experiment was performed to detect the motion of an adult moving in a room (FIG. 9). We then measured the response of the smaller sample to movements in- and off-axis of a hotplate held at constant temperature, located 33 cm away from the sample (FIG. 5B). The smaller sample was also sensitive to variations in the position of the hotplate.

Cyberwood is an example of how plant nanobionics (Giraldo et al. (2014), *Nat Mater* 13(4):400-408) can be exploited to create novel materials with record high temperature sensitivity.

TABLE 1

| Moisture, % | Temperature T, ° C. | Resistance R, Ω | Response, $K^{-1}$ |
|---|---|---|---|
| 0 | 73.53 | $1.51 \cdot 10^7$ | 17.26 |
|   | 35.53 | $9.92 \cdot 10^9$ |   |
| 2.2 | 74.74 | $7.55 \cdot 10^6$ | 17.26 |
|   | 34.49 | $5.26 \cdot 10^9$ |   |
| 3.8 | 73.78 | $3.89 \cdot 10^6$ | 14.45 |
|   | 36.00 | $2.13 \cdot 10^9$ |   |
| 4.4 | 74.44 | $1.90 \cdot 10^6$ | 10.12 |
|   | 35.29 | $7.53 \cdot 10^8$ |   |
| 5.7 | 74.08 | $5.20 \cdot 10^5$ | 13.10 |
|   | 35.22 | $2.65 \cdot 10^8$ |   |

Temperature Response

Table 1 shows the calculation of an effective TCR coefficient $(\Delta R/R)/(\Delta T)$ from experimental data in FIG. 4A. Note that the TCR values are calculated over a 40° C. temperature interval (i.e., between the maximum and minimum temperatures in the experiments shown in FIG. 4A).

Measurements of Dehydration

The larger samples were held for a finite time at 75° C. (see FIG. 4B and FIG. 7A). The current-voltage (I-V) characteristics of these samples were monitored with three different moisture contents, both at the beginning and at the end of the temperature hold. As expected, the two curves (representing samples with a 0% moisture level) overlap, confirming that the sample could not be dried further at this temperature. The results also demonstrate that the samples are stable in a broad range of voltages.

To show that the dehydration process was reversible the samples were re-hydrated keeping them at room temperature for 10 days and the I-V measurements were repeated. It was found that the re-hydrated samples had 6.7% moisture content. FIG. 7B shows the I-V curves at room temperature before cycling (5.7% moisture, 317 mg) and after rehydration (6.7%, 320 mg). Both characteristics are linear. No current was measured at 0 applied voltage.

Comparison with Other CNT-Based Temperature Sensors

Sensors composed of CNTs interspersed in a polymeric matrix can detect temperature variations because the CNT-CNT tunneling junctions are sensitive to strain variations (Alamusi et al. (2013), *Nanotechnology* 24(45):455501). Percolation of nano-composites through a two-dimensional area has been modeled (Li et al. (2007), *Appl Phys Lett* 90:174108). More specifically, the role of tunneling resistance in the electrical conductivity of CNT-based composites was analyzed in Li et al. (2007), *Appl Phys Lett* 90:223114. In this work, CNTs at a contact point in the network were assumed to overlap. The tunneling resistance of CNT-polymer matrix composites depends on the material of the insulating layer and on its thickness. Simmons J G (1963), *J Appl Phys* 34:1793, derived a general formula for the electric tunneling effect between similar electrodes separated by a thin insulating film. When the thickness of the insulating layer between crossing CNTs is uniform and the variation of the barrier height along the thickness can be neglected, the formula for a rectangular potential barrier can be employed. Therefore, the current density inside the insulating layer can be expressed according to Simmons J G (1963), *J Appl Phys* 34:1793, and Li et al. (2007), *Appl Phys Lett* 90:223114, as a function of the thickness of the insulating layer and the height of the rectangular barrier. The latter is approximately taken as the work function of CNTs in V Li et al. (2007), *Appl Phys Lett* 90:223114, and the dielectric constant of the insulating material.

It has been shown that the thickness of the insulating layer between crossing CNTs plays a significant role in the tunneling resistance, which increases very rapidly with increasing thickness (Li et al. (2007), *Appl Phys Lett* 90:223114). Further, tunneling occurs only if t<18 Å (Li et al., (2007), *Appl Phys Lett* 91:223114; Balberg (1987), *Phys Rev Lett* 59(12):1305-1308). The change of the height of the barrier with temperature has been introduced recently by Alamusi et al. (2013), *Nanotechnology* 24(45):455501, to model the high performance temperature sensing of a MWCNT/epoxy nanocomposite. The sensitivity of this MWCNT/epoxy nanocomposite increased with increasing MWCNTs content. The largest value of the TCR reported was 2.1% $K^{-1}$, corresponding to a loading of 5% wt of MWCNTs (Alamusi et al. (2013), *Nanotechnology* 24(45):455501). In this material, the resistance was found to increase with temperature (Alamusi et al. (2013), *Nanotechnology* 24(45):455501). The opposite behaviour was found for MWCNTs/epoxy material with 0.5% wt MWCNTs content (Neitzert et al. (2011), *IEEE Trans NanoTechnol* 10(4):688-693). In this case, the resistance decreased with increasing temperature and a TCR of −0.06% $K^{-1}$ was reported (Neitzert et al. (2011), *IEEE Trans NanoTechnol* 10(4):688-693). A TCR of 0.2% $K^{-1}$ was measured for a pure 2-D MWCNT network deposited on top of aluminium electrodes (Di Giacomo et al. (2014), *Can J Phys* 92(7/8):827-831). The sensitivity of suspended pure SWCNTs in vacuum was also reported earlier and was found to be larger than that of pure MWCNTs, but similar to that of vanadium dioxide (Itkis et al. (2006), *Science* 312(5772):413-416). In those experiments the measured TCR was −2.5% $K^{-1}$ in the 100 to 330 K temperature range (Itkis et al. (2006), *Science* 312(5772):413-416, Itkis et al. (2007), *Nano Lett* 7(4):900-904).

Composite materials obtained with MWCNTs and fungal cells grown in suspension were fabricated earlier (Di Giacomo et al. (2013), *IEEE Trans NanoTechnol* 12(6):1026-1030; Di Giacomo et al. (2013) *IEEE Trans NanoTechnol* 12(2):111-114). However, fungal cells do not contain pectin in their cell wall, so their behaviour is expected to be different from that of plant cell/MWCNTs composites. Materials composed of *C. albicans* and MWCNTs were shown to have a TCR of 0.1% $K^{-1}$. This response was due to the presence of MWCNTs alone (Di Giacomo et al. (2013) *IEEE Trans NanoTechnol* 12(2):111-114). In cyberwood, MWCNTs are not centrally responsible for the ultra-high temperature response. Nevertheless, their percolation path through cellulose microfibrils increases the current transmitted in the material and stabilizes its response. This phenomenon is due to conduction through tunneling junctions between MWCNTs with cellulose microfibrils, acting as insulator.

Comparison with CNT/Cellulose Humidity Sensors

Humidity sensors based on CNTs and cellulose have been described previously (Qi et al. (2013), *Sens Actuators B Chem* 185:225-230). However, their behaviour is very different from cyberwood. Qi et al. (2013), *Sens Actuators B Chem* 185:225-230, have shown that when a CNT/cellulose composite sensor was immersed in water, resistance increased whilst it decreased upon drying. This phenomenon was attributed to the swelling of the cellulose matrix in the presence of water (Qi et al. (2013), *Sens Actuators B Chem* 185:225-230). A humidity sensor with cellulose paper was also produced using single walled CNTs functionalized with carboxylic acid (Han et al. (2012), *J Phys Chem C* 116(41): 22094-22097). Also in this case, the resistance increased upon increasing the relative ambient humidity, in contrast to the electrical properties of cyberwood. However, similarly to cyberwood, the conductivity of bare paper increased while increasing humidity content. The explanation is in accordance with our results: water dissociation occurs on the moist cellulose fibres under an applied bias, dissociating $H^+$ and $OH^-$ ions. Thus, the current flow is due to ionic conduction (Han et al. (2012), *J Phys Chem C* 116(41): 22094-22097).

Effect of a Polymeric Housing on the Properties of Cyberwood

For practical applications, a housing was introduced (wrapping the sensor in a cellophane film) around the cyberwood to shield the material from the effect of ambient humidity. Additional experiments have been performed to show the effect of a polymeric housing on the temperature response of cyberwood. A cyberwood sensor was encased in a polymeric housing and placed in an oven kept at constant temperature (21° C.). The ambient humidity was increased from 44 to 82% using an ultrasonic humidifier. The ambient humidity was monitored at all times with a humidity CMOS sensor (Sensirion). As shown in FIG. 8, cyberwood enclosed in a polymeric housing was not sensitive to humidity changes. However, the presence of the housing did not alter the ultra-high temperature response, as shown in the inset of FIG. 8.

Temperature Sensitivity at Distance

Experiments were performed to detect the motion of an adult moving in the room where the sensor was positioned. The sensor detected accurately the motion of the person who was moving closer to the sensor every 30 s (from 80 to 40 cm) and held still for additional 20 s at each position. As expected, the measured current increased with decreasing distance of the body from the sensor. In between measurements, the person moved away from the sensor for ca. 10 s. Every time the person left the current diminished towards the reference value at 23° C. During the experiments, the air temperature near the cyberwood sensor was monitored with an independent thermometer (a calibrated platinum-resistance temperature detector). The independent air temperature measurements are shown in FIG. 9.

Example 2

Synthetic skins (Sun et al. (2014), *Adv. Mater.* 26, 7608-7614) are essential to augment robotics (Kaltenbrunner et al. (2013), *Nature* 499, 458-463) and improve the performance of prosthetic limbs (Kim et al. (2014), *Nature Commun.* 5, 5747). Some flexible devices emulate properties of the human skin, such as wound healing (Tee et al. (2012), *Nature Nanotech.* 7, 825-832), response to pressure, strain (Kim et al. (2014), *Nature Commun.* 5, 5747) and temperature variations (Segev-Bar et al. (2013), *ACS Appl. Mater. Interfaces* 5, 5531-5541). Human skin monitors temperature with very high sensitivity, via voltage-gated ionic-channel transmembrane proteins (Vay et al. (2012), *British J. of Pharmacol.* 165, 787-801), and presents different spatial density of thermosensitive receptors in different areas of the body (Nadel et al. (1973), *Pflügers Arch.* 340, 71-76 (Springer-Verlag)). However, the temperature sensitivity of existing materials is low. In addition, synthetic skins are limited in their differential temperature sensitivity, because the expansion of their pixel density requires a linear increase of the number of sensors and flexible electrical connections. This makes the fabrication and use of current synthetic skins rather cumbersome. Here, we describe an iontronic hydrogel with extremely high temperature sensitivity. We fabricated transparent thermometers and self-standing, flexible films. By depositing electrodes only on the outer frame of the films, we created skins with pixel-by-pixel temperature sensitivity with different spatial resolutions. The number of electrical contacts required is proportional to the square root of the pixel density. These devices are ultra-low cost, biocompatible, and can be used as sensitive layers to monitor heat transfer on surfaces.

Hydrogels are soft, transparent materials widely used in everyday life, as thickening agents in food science (Saha et al. (2010), *J. Food Sci. Technol.* 47, 587-597), for contact lenses (Stapleton et al. (2006), *Ocular Surf.* 4, 24-43), wound healing skins (Miguela et al. (2014), *Carb. Polym.* 111, 366-373) in medicine, and drug releasers in cosmetics (McCrudden et al. (2015), *Exp. Dermatol.* 24, 561-566). More recently, the ionic conductivity of hydrogels has been exploited in stretchable electrical contacts (Keplinger et al. (2013), *Science* 341, 984-987). However, hydrogels have never been used so far as active materials to create flexible, biocompatible and transparent temperature sensors.

It has been shown previously that the combination of dehydrated plant cells and CNTs forms a material (Di Giacomo et al. (2013), *IEEE Trans.* 12, 1026-1030), cyberwood, with exceptionally high temperature response (Di Giacomo et al. (2015), *PNAS* 112, 4541-4545; Wilson (2015), *Phys. Today* 68, 15). Further, it has been suggested that this response is due to the available $Ca^{2+}$ ions present in pectin molecules of the plant cell wall (Di Giacomo et al. (2015), *PNAS* 112, 4541-4545). Here, we show that a pectin hydrogel sensor has responsivity comparable to cyberwood, which further supports the mechanism governing its temperature sensitivity.

Pectin, a component of all higher plant cell walls is made of structurally and functionally very complex, acid-rich polysaccharides (Sriamornsak (2003), *Silpakorn Univ. Int. J.* 3, 206-228). Pectin plays several roles in plant growth among which development, morphogenesis, defense, cell-cell adhesion, cell wall structure and porosity, binding of ions, enzymes, pollen tube growth and fruit development (Willats et al. (2001), *Plant Mol. Biol.* 47, 9-27). In high-ester pectins, at acidic pH, individual pectin chains are linked together by hydrogen bonds and hydrophobic interactions. Contrary, in low-ester pectins, close to neutral pH, ionic bridges are formed between $Ca^{2+}$ ions and the ionized carboxyl groups of the galacturonic acid, generating the so-called "egg box" (Plazinski (2011), *J. Comput. Chem.* 32, 2988-95). Since gelation rate of pectin decreases exponentially with temperature (Cardoso et al. (2003), *Food Hydrocoll.* 17, 801-807) increasing the temperature of a $Ca^{2+}$ crosslinked pectin, the number of free ions available for electrical conduction increases (Di Giacomo et al. (2015), *PNAS* 112, 4541-4545). High dependence of current with temperature is expected in pure pectin samples as well.

We created a bulk gel embodying water, pectin and $CaCl_2$ (see Methods section). We cut a fragment of gel and placed it on top of two gold plated electrodes (0.47 mm×0.47 mm×2.75 mm, 0.72 mm apart) and dehydrated it (FIG. 10A). After dehydration we soaked the sample in liquid polydimethylsiloxane (PDMS) to protect it from environmental humidity.

The sample was dehydrated until the measured absolute water content was reduced to 30%. Above this value the electrical conductivity of water is predominant and the total conductivity of the hydrogel measured is in the order of 28 $mSm^{-1}$. Upon dehydration the electrical conductivity associated with water decreases, thus the conductivity of pectin is predominant. The conductivity of the hydrogel after dehydration is in the order of 0.1 $mSm^{-1}$. After dehydration the current is stable at a given temperature. FIG. 10B shows a schematic representation of the pectin network, calcium ions and water molecules in the low water content regime. As temperature increases the number of dissociated chains of polygalacturonic acid (black lines) increases and thus the number of free $Ca^{2+}$ ions. FIG. 13 shows that the current-voltage characteristic of a typical sample is linear. Samples were then heated on a plate increasing the temperature from 8 to 39° C. following two temperature steps as reported in FIG. 14. Current was monitored when 20 V were applied. The curve was obtained by sampling current and temperature every 1 second up to 30° C. and every 4 second up to 39° C. The thermal responsivity is comparable to that of cyberwood (Di Giacomo et al. (2015), *PNAS* 112, 4541-4545). The inset in FIG. 10C represents the equivalent electrical model for the pectin thermistor. FIG. 14B shows the Arrhenius plot of conductivity whose activation energy of 83 kJ/mol was calculated from the slope. The value is in agreement with the activation energy reported for rheological measurements (Cardoso et al. (2003), *Food Hydrocoll.* 17, 801-807).

To exploit the high temperature responsivity of the material we fabricated thin films casting a pectin solution inside a frame on an electrically insulating substrate. We immersed the casted liquid in a 32 mM $CaCl_2$ solution and allowed it to jellify overnight. We removed the gel from the solution, and dehydrated it (see Methods section). We fabricated films ~200 μm thick. FIG. 11A shows the setup we used to monitor temperature and current variations of all samples. A thermal camera was employed to monitor the local temperature of the samples while their electrical current was measured via an independent source meter. The photograph in FIG. 11B shows the transparent film and the electrical contacts: the steel clamps are in direct contact with the film. FIG. 11C shows a thermal image of the film, which is not transparent to radiated heat. FIG. 11D shows on the left axis the current increase in the film and, on the right axis, the temperature monitored by the thermal camera proving that current and temperature match. Details of small variations are reported in FIG. 11E by zooming the square of FIG. 11D at 2 second interval. We also repeated the experiment with carbon electrodes and no difference in the behaviour was found, excluding any effect due to the interaction of the gel with a metal. These measurements demonstrated that pectin hydrogel films sense minor temperature variations.

FIG. 12 shows transparent, flexible temperature-sensing skins with electrodes only on the external frame. FIG. 12A, B show photographs of pectin films sandwiched between two PDMS layers with chromium/gold electrical contacts. FIG. 12C shows schematics of the section of the device. The current was monitored at all rows and columns while a finger touched one of the 4 pixels for ~2 sec. Current measurements were acquired using the circuit shown in FIG. 16 and values converted into a voltage. The bottom insulator was $SiO_2$ and the top PDMS. The acquisition rate was 100 samples per second corresponding to 25 samples per second per channel. The current was averaged on 5 samples per channel. Panels on the sides of the drawing in FIG. 12D represent the percentage of voltage increase upon touching pixel $P_{11}$ as a function of time. The greyscale-coding squares represent the product between the maximum percentages of voltage variations detected at each row and column. Table 1 represents the values of the products corresponding to the greyscale coding bar in FIG. 12D. For each pixel touched the maximum product value was normalized to 1. FIG. 17 shows the increase in voltage percentage over time for each of the 4 pixels when individually touched.

To confirm that the noise in FIG. 17 is due to the electronic readout circuit of FIG. 16, we performed a similar measurement with a pico-ampere meter and the corresponding noise free curve is reported in FIG. 18 in which the current of a single row was measured when a single pixel was touched for less than 1 sec. The temperature variation on the pixel was estimated to be less than 1 K as shown in the thermal image in FIG. 19. FIG. 20 shows that the sensing phenomenon is due to temperature variations since the sample's measurement did not exhibit a significant change when pressed for few seconds by a metal object at the same temperature of the pixel. On the contrary, current increased significantly when touched with a finger for the same length of time. FIG. 21 displays the thermal image of a 16-pixel device immediately after an aluminium square was placed on it at 26° C. The experiment was performed at an ambient temperature of 20° C. FIG. 12E shows the row and column product as in FIG. 12D for each of the 16 pixels 0.8 seconds after the aluminium square was laid in contact with the skin. The acquisition rate was 10 samples per second corresponding to 1.25 samples per second per channel. Table 2 reports the corresponding values. FIG. 12F shows the pixelated thermal image acquired by the thermal camera reported in FIG. 21. Each pixel is considered as the intersection between each row and column according to the electrode position.

TABLE 2

|  | C1 | C2 | C3 | C4 |
|---|---|---|---|---|
| R1 | 0.45 | 0.49 | 0.59 | 0.59 |
| R2 | 0.59 | 0.63 | 0.76 | 0.76 |
| R3 | 0.77 | 0.82 | 1.00 | 0.99 |
| R4 | 0.74 | 0.79 | 0.96 | 0.95 |

These experiments demonstrate that the density of sensitive pixels can be intensified simply by increasing the number of electrodes on the external frame of the film. For 16 pixels we used 16 contacts instead of 32, differently from existing technologies that require the use of complex wiring to ensure at least 2 contacts at each pixel site and a network of thin film transistors. This is feasible for the extremely high thermal sensitivity of the hydrogel skin (see also FIG. 16).

We reported that the use of hydrogels for temperature sensing on all kinds of surfaces has several advantages: a state of the art extreme temperature sensitivity, transparency, ultra-low cost, and ease of manufacturing. Further just a simple contact geometry and a straightforward readout circuit is required.

TABLE 3

| P11 | C1 | C2 | P12 | C1 | C2 |
|---|---|---|---|---|---|
| R1 | 1 | 0.4 | R1 | 0.4 | 1 |
| R2 | 0.6 | 0.2 | R2 | 0.2 | 0.5 |
| P21 | C1 | C2 | P22 | C1 | C2 |
| R1 | 0.5 | 0.2 | R1 | 0.3 | 0.51 |
| R2 | 1 | 0.5 | R2 | 0.5 | 1 |

FIG. 22 shows a typical thermal response measured at three different frequencies on the small pectin film samples shown in FIG. 10a. The current is reported in arbitrary units since it was measured as the RMS value of the voltage drop on a resistor (50 k$\Omega$) in series with the sample (see inset of FIG. 22). The electrical measurements were acquired with a lock-in amplifier model SR830 Stanford research systems. No responsivity difference between measurements at different frequencies and d.c. measurements was found.

FIG. 23a shows a typical current in a pectin film sample when the temperature is cycled for 6 h between 20 and 26° C. The material responds stably and the responsivity matches with FIG. 10c. FIG. 23b shows a 2 cycles zoom. The current in FIG. 23 was measured with a Keithley 2336B source meter. The applied voltage was a square wave with an amplitude of 20 V and a frequency of 1 Hz. The sampling rate was 8 samples per second. Temperature on the film was actuated by a Peltier element QC-31-1.4-8.5M. Independent temperature measurements on the film were measured with a Pt100 platinum thermometer.

The invention claimed is:

1. A temperature sensor comprising
    a sensor gel comprising a polymer, water (>0.1%), and ions at a concentration of 1 pM or more, and
    a first electrode and a second electrode separated from each other by said sensor gel.

2. The temperature sensor of claim 1, wherein said polymer is a polyelectrolyte.

3. The temperature sensor of claim 1, wherein said polymer is selected from
    (a) a charged biopolymer, and/or
    (b) a synthetic polymer having charged moieties.

4. The temperature sensor of claim 3, wherein the charged biopolymer comprises a peptide, a polypeptide, or a polysaccharide comprising charged moieties.

5. The temperature sensor of claim 3, wherein the charged biopolymer comprises pectin, alginate, or alginate sulfate.

6. The temperature sensor of claim 3, wherein the synthetic polymer comprises polyacrylic acid, polysterene sulfonate, a cationic derivate of hyaluronic acid, or carboxymethyl cellulose.

7. The temperature sensor of claim 1, wherein said polymer is selected from
an uncharged polysaccharide, or
an uncharged peptide or polypeptide.

8. The temperature sensor of claim 7, wherein the uncharged polysaccharide comprises agarose, amylase, amylopectin, callose, cellulose, chitin, chitosan, dextran, glycogen, guaran, or hemicellulose.

9. The temperature sensor of claim 1, wherein said ions have a charge of 2 or greater.

10. The temperature sensor of claim 9, wherein said ions are $Ca^{2+}$, $Mg^{2+}$, $Cu^{2+}$, $Sr^{2+}$, or $Ba^{2+}$ ions.

11. The temperature sensor of claim 10, wherein said ions are $Ca^{2+}$ ions.

12. The temperature sensor of claim 1, wherein said sensor gel has a water content of <60%.

13. The temperature sensor of claim 12, wherein the water content is <40% weight per weight.

14. The temperature sensor of claim 12, wherein the water content is <30% weight per weight.

15. The temperature sensor of claim 1, wherein the stoichiometric ratio of ions to charged moieties of said polymer is 1:1000 to 3:1.

16. The temperature sensor of claim 15, wherein the stoichiometric ratio of ions to charged moieties of said polymer is 1:100 to 3:1.

17. The temperature sensor of claim 15, wherein the stoichiometric ratio of ions to charged moieties of said polymer is 1:10 to 3:1.

18. The temperature sensor of claim 15, wherein the stoichiometric ratio of ions to charged moieties of said polymer is 1:1.

19. The temperature sensor of claim 1, wherein said sensor gel is a cell free gel.

20. The temperature sensor of claim 19, wherein the sensor gel is essentially composed of said polymer, water, and ions.

21. The temperature sensor of claim 20, wherein said sensor is free from carbon nanotubes.

22. The temperature sensor of claim 1, wherein said sensor gel is embedded in a casing that is not permeable to liquid water and/or water vapour.

23. The temperature sensor of claim 22 wherein said casing is transparent to infrared radiation.

24. The temperature sensor of claim 23 wherein said infrared radiation has a wavelength range of 3 µm to 50 µm.

25. A system comprising
(a) the temperature sensor according to claim 1,
(b) a voltage source or electric current source,
(c) a measurement device for detecting voltage or electric current,
wherein said temperature sensor and said measurement device are connected, such that an electric current through said temperature sensor or a voltage between said first electrode and said second electrode is measurable by said measurement device.

26. A bolometer, wherein said bolometer comprises the temperature sensor according to claim 1.

27. The bolometer of claim 26, wherein the bolometer is a mid or far infrared detector.

28. A temperature sensor array comprising a plurality of sections arranged in a two-dimensional array, wherein each section comprises the respective temperature sensor according to claim 1, and wherein the temperature of each section is determinable by means of said respective temperature sensor.

29. A method for temperature detection by means of a temperature sensor according to claim 1, wherein the method comprises the steps of
(a) providing the temperature sensor according to claim 1,
(b) providing a voltage or an electric current between said first electrode and said second electrode of said temperature sensor,
(c) measuring an electric current or a voltage between said first electrode and said second electrode, and
(d) determining a temperature from said measured electric current or voltage.

30. The method according to claim 29, wherein infrared radiation of an object is detected by means of said temperature sensor.

31. The temperature sensor of claim 1, wherein the sensor gel comprises water (10-40%).

* * * * *